United States Patent
Vinogradov et al.

(10) Patent No.: US 9,555,132 B2
(45) Date of Patent: Jan. 31, 2017

(54) WATER-SOLUBLE NANOPARTICLES

(71) Applicant: The Trustees of the University of Pennsylvania, Philadelphia, PA (US)

(72) Inventors: Sergei A. Vinogradov, Wynewood, PA (US); Tatiana V. Esipova, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 486 days.

(21) Appl. No.: 13/921,540

(22) Filed: Jun. 19, 2013

(65) Prior Publication Data

US 2014/0004048 A1     Jan. 2, 2014

Related U.S. Application Data

(60) Provisional application No. 61/662,135, filed on Jun. 20, 2012, provisional application No. 61/787,316, filed on Mar. 15, 2013.

(51) Int. Cl.
| | |
|---|---|
| *A61K 9/14* | (2006.01) |
| *A61K 49/12* | (2006.01) |
| *G01N 33/58* | (2006.01) |
| *A61K 49/18* | (2006.01) |

(52) U.S. Cl.
CPC ......... *A61K 49/124* (2013.01); *A61K 49/1857* (2013.01); *G01N 33/587* (2013.01); *Y10T 428/2982* (2015.01)

(58) Field of Classification Search
CPC .................................................. A61K 49/124
See application file for complete search history.

(56) References Cited

U.S. PATENT DOCUMENTS

| | | | | |
|---|---|---|---|---|
| 2011/0021970 A1* | 1/2011 | Vo-Dinh | ............ | A61K 49/0039 604/20 |
| 2011/0294987 A1* | 12/2011 | Kanazaki | ............... | C07K 17/08 530/391.3 |
| 2012/0220051 A1* | 8/2012 | Yin | ...................... | G01N 33/558 436/501 |

FOREIGN PATENT DOCUMENTS

WO     WO 2004031732 A2 *   4/2004   ............. C09K 11/02

OTHER PUBLICATIONS

Ye et al., "Morphologically controlled synthesis of colloidal upconversion nanophosphors and their shape-directed self-assembly" 2010, PNAS, vol. 107, pp. 22430-22435.
Mader et al., "Upconverting luminescent nanoparticles for use in bioconjugation and bioimaging" 2010, Current Opinion in Chemical Biology, vol. 14, pp. 582-596.

* cited by examiner

*Primary Examiner* — Paul Dickinson
(74) *Attorney, Agent, or Firm* — Mark S. Cohen; Pearl Cohen Zedek Latzer Baratz LLP

(57) ABSTRACT

The invention relates to water-soluble nanoparticles and methods for making such nanoparticles. Specifically, the invention relates to dendrimerization to enhance the solubility of nanoparticles.

32 Claims, 15 Drawing Sheets

Scheme 1

Scheme 3

WATER-SOLUBLE NANOPARTICLES

CROSS REFERENCE TO RELATED APPLICATIONS

This application claims the benefit of U.S. Ser. No. 61/787,316, filed on Mar. 15, 2013 and of U.S. Ser. No. 61/662,135, filed on Jun. 20, 2012, both of which are incorporated by reference herein in their entirety.

FIELD OF THE INVENTION

The invention relates to water-soluble nanoparticles and methods for making such nanoparticles. Specifically, the invention relates to dendrimerization to enhance the solubility of nanoparticles.

BACKGROUND OF THE INVENTION

Colloidal up-converting nanoparticles (UCNPs) are capable of converting near-infrared excitation into visible emission via mutiphoton up-conversion processes. These processes involve long-lived excited electronic states of dopant lanthanide ions—antennae (e.g. $Yb^{3+}$), admixed to the crystal lattices of host materials (e.g. NaYF4). The host crystals also contain emissive lanthanide ions—emitters (e.g. $Er^{3+}$). The antenna ions transfer excitation energy onto the emitter ions by way of multi-exciton annihilation/sensitization process. The overall up-conversion scheme consist of the following steps: 1) excitation of two or more antenna ions by low energy photons, 2) diffusion of the excitons mediated by energy transfer/exchange between the antenna ions, 3) formation of multi-exciton antenna/emitter complexes; 4) exciton annihilation and sensitization of excited states of the emitter ions within these complexes, followed by 4) emission of a higher energy photon. These processes, occurring at the core of the UCNP, are responsible for its photophysical properties, which are relatively insensitive to the environment. On the contrary, the periphery of the particle, which remains in constant contact with the environment, determines the UNCP biocompatibility and bioanalytical functionality.

UCNPs offer a number of advantages for biological imaging, including high photostability, narrow emission bands, near infrared excitation wavelengths for depth-resolved imaging and potentially reduced risk of photodamage. Compared to conventional multiphoton excitation, sequential absorption of photons by UCNPs occurs via population of real as opposed to virtual states; and, therefore, multiphoton excitation cross-sections of UCNPs are much higher than those of regular organic dye molecules. In fact, multiphoton excitation and emission of UCNPs can be induced by low power continuous wave (cw) sources. Such sources excite virtually zero auto-fluorescence and cause no photodamage.

There have been many efforts to utilize UCNPs in biological sensing. UCNPs can be effectively detected at cm's depths in the tissue, including applications in optical tomography, as well as provide opportunities for single-particle detection. Multicolor nature of UCNP emission has been recently demonstrated as a valuable tool for in vivo imaging. Nonetheless, all so far reported experiments capitalize on the advantage of near-infrared excitation to induce emission of UCNPs, whereas very few specific biological analytes have been addressed, e.g. lectin. Furthemore, in spite of the fact that the multiphoton-nature of UCNP excitation is a natural prerequizite for multiphoton microscopy applications, no high-resolution depth-resolved imaging using UCNPs has yet been performed.

UCNPs can be synthesized by a variety of methods. In the majority of these synthetic schemes, and especially in those schemes that yield the maximally emissive nanoparticles (vide infra), UCNPs are stabilized by coats of the so-called supporting ligands, such as oleic acid, polyethyleneamine etc, or even by secondary inorganic shells (e.g. mesoporous silica).

The role of this layer is to control the formation of nanocrystals, keep the UCNPs in solution during the synthesis and maximize the yield of a particular crystalline phase (β- or hexagonal phase), which is characterized by the highest up-conversion efficiency. The supporting organic ligands are attached to the UCNP surfaces by their polar head groups (carboxyls or amines). The long hydrophobic tails support crystals in non-polar solutions, but make them completely insoluble in aqueous environments. For biological applications these ligands shoul be replaced by hydrophilic coats to ensure high aqueous solubility.

Solubilization of UCNPs in aqueous environments has been attempted by several methods, including solvothermal, hydrothermal, ionothermal methods and the method of thermal decomposition. These methods differ in their efficiency and generality, but presently there is no universal approach to the synthesis of truly water-soluble UCNPs with surface groups suitable for functionalization and linking to biological targets.

Accordingly, there exits a need for improved nanoparticles that would provide enhanced solubility in water.

SUMMARY OF THE INVENTION

In one embodiment, the invention provided herein relates to a composition comprising a plurality of nanoparticles, wherein the surface of each nanoparticle is dendrimerized by operably linking to a dendrite polymer having a hydrophilic group or a hyperbranched polymer having a hydrophilic group, and wherein said composition is water-soluble. In one exemplary embodiment, the hydrophilic group is ionic. In an exemplary embodiment, the nanoparticle is an up-converting nanoparticle.

In another embodiment, the invention provides an imaging agent comprising a plurality of nanoparticles, wherein the surface of each nanoparticle is dendrimerized by operably linking to a dendrite polymer having a hydrophilic group or a hyperbranched polymer having a hydrophilic group, and wherein said composition is water-soluble. In one exemplary embodiment, the hydrophilic group is ionic.

In another embodiment, the invention provided herein relates to a method for enhancing the solubility of nanoparticles, the method comprising: providing a plurality of nanoparticles; dendrimerizing the surface of each nanoparticle by operably linking to a dendrite polymer having a hydrophilic group or a hyperbranched polymer having a hydrophilic group; obtaining the dendrimerized nanoparticles, thereby enhancing the solubility of said nanoparticles. In one exemplary embodiment, the hydrophilic group is ionic.

In another embodiment, the invention provided herein relates to a method for obtaining or synthesizing water-soluble nanoparticles, the method comprising: providing a plurality of nanoparticles; dendrimerizing the surface of each nanoparticle by operably linking to a dendrite polymer having a hydrophilic group or a hyperbranched polymer having a hydrophilic group; obtaining the dendrimerized nanoparticles, thereby obtaining said water-soluble nanoparticles. In one exemplary embodiment, the hydrophilic group is ionic.

In another embodiment, the invention provided herein relates to a method for producing a composition of nanoparticles, comprising the steps of: providing a plurality of nanoparticles; dendrimerizing the surface of each nanoparticle by operably linking to a dendrite polymer having a hydrophilic group or a hyperbranched polymer having a hydrophilic group; obtaining the dendrimerized nanoparticles; functionalizing the dendrimerized nanoparticles with a target agent, thereby producing said composition of nanoparticles. In one exemplary embodiment, the hydrophilic group is ionic.

In another embodiment, the invention provided herein relates to a method of obtaining an image in a subject, comprising administering to said subject a composition comprising a plurality of nanoparticles, wherein the surface of each nanoparticle is dendrimerized by operably linking to a dendrite polymer having a hydrophilic group or a hyperbranched polymer having a hydrophilic group, and wherein said dendrite polymer or said hyperbranched polymer facilitates the solubility of said nanoparticles; imaging said subject, thereby obtaining said image in said subject.

In one embodiment, the invention provided herein relates to a method of measuring the presence of an analyte in a sample, the method comprising contacting said sample with a composition comprising a plurality of nanoparticles, wherein the surface of each nanoparticle is dendrimerized with a plurality of dendrite polymers having a hydrophilic group or a hyperbranched polymer having a hydrophilic group, and wherein said dendrite polymers or hyperbranched polymers comprise an analyte-sensitive core that signals the presence of said analyte, thereby measuring the presence of the analyte in said biological sample. In one exemplary embodiment, the hydrophilic group is ionic.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

The invention provides water-soluble nanoparticles and methods for making such nanoparticles. Specifically, the invention provides dendrimerization to enhance the solubility of nanoparticles.

In one embodiment, provided herein is a composition comprising a plurality of water-soluble nanoparticles, wherein the surface of each nanoparticle is dendrimerized by operably linking to a dendrite polymer or a hyperbranched polymer having a hydrophilic ionic group, and wherein said dendrite polymer or said hyperbranched polymer facilitates the solubility of said nanoparticles. In an exemplary embodiment, the nanoparticle is an up-converting nanoparticle.

In another embodiment, provided herein is an imaging agent comprising a plurality of water-soluble nanoparticles, wherein the surface of each nanoparticle is dendrimerized by operably linking to a dendrite polymer or a hyperbranched polymer having a hydrophilic ionic group, and wherein said dendrite polymer or said hyperbranched polymer facilitates the solubility of said nanoparticles.

In another embodiment, provided herein is a method for enhancing the solubility of nanoparticles, the method comprising: providing a plurality of nanoparticles; dendrimerizing the surface of each nanoparticle by operably linking to a dendrite polymer or a hyperbranched polymer having a hydrophilic ionic group; obtaining the dendrimerized nanoparticles, thereby enhancing the solubility of said nanoparticles. In another embodiment, provided herein is a method for obtaining or synthesizing water-soluble nanoparticles, the method comprising: providing a plurality of nanoparticles; dendrimerizing the surface of each nanoparticle by operably linking to a dendrite polymer or a hyperbranched polymer having a hydrophilic ionic group; obtaining the dendrimerized nanoparticles, thereby obtaining said water-soluble nanoparticles. In another embodiment, provided herein is a method for producing a composition of nanoparticles, comprising the steps of: providing a plurality of nanoparticles; dendrimerizing the surface of each nanoparticle by operably linking to a dendrite polymer or a hyperbranched polymer having a hydrophilic ionic group; obtaining the dendrimerized nanoparticles; functionalizing the dendrimerized nanoparticles with a target agent, thereby producing said composition of nanoparticles.

In another embodiment, provided herein is a method of obtaining an image in a subject, comprising administering to said subject a composition comprising a plurality of water-soluble nanoparticles, wherein the surface of each nanoparticle is dendrimerized by operably linking to a dendrite polymer or a hyperbranched polymer having a hydrophilic ionic group, and wherein said dendrite polymer or said hyperbranched polymer facilitates the solubility of said nanoparticles; imagining said subject, thereby obtaining said image in said subject.

Figure 8:
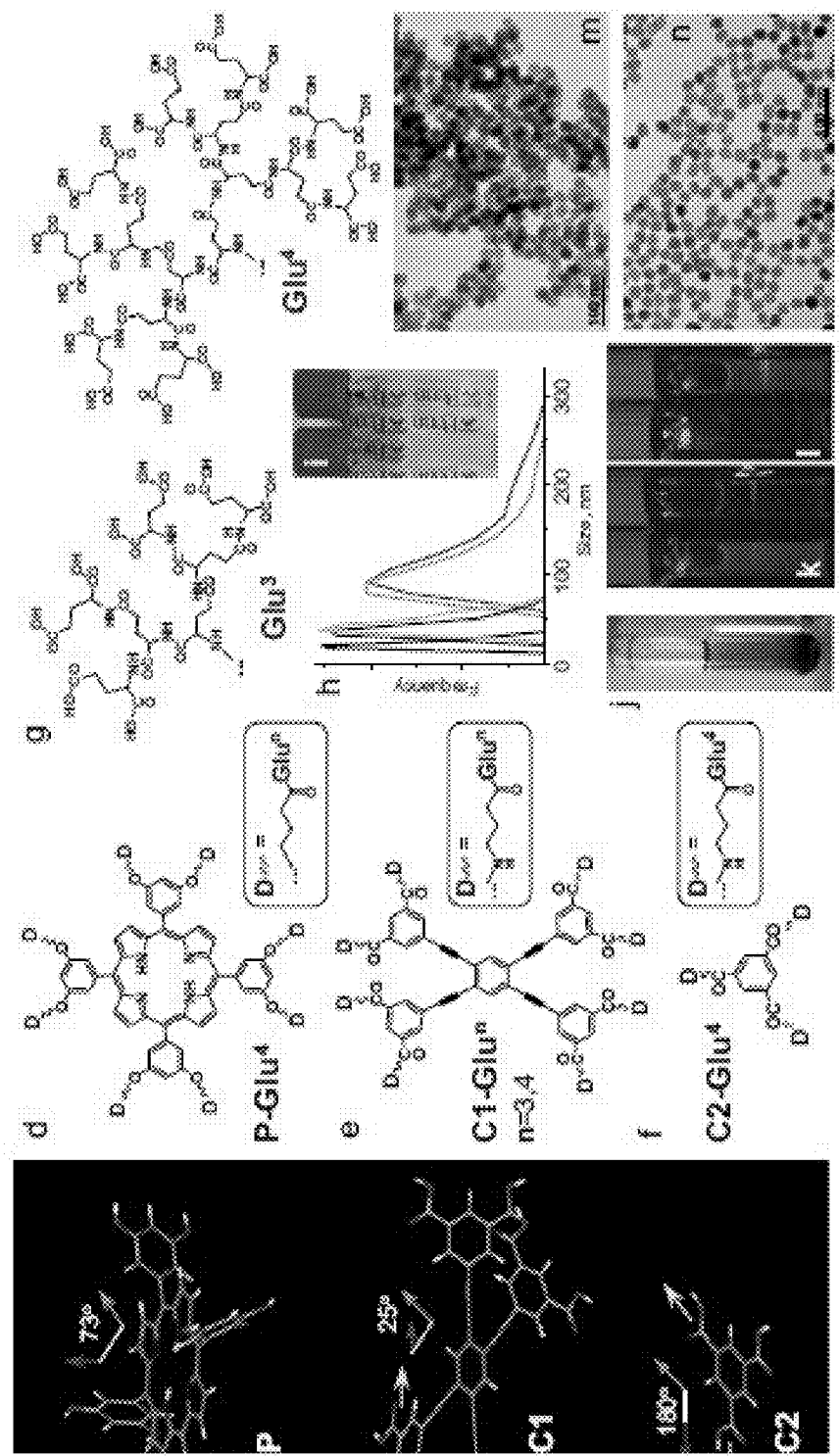
FIG. 8 shows (A-C) structures of cores P (eight anchor groups), C1 (eight anchor groups), and C2 (three anchor groups) used for construction of dendrimers. Dihedral angles show orientation of the planes containing anchor groups relative to the core. (D-F) Polyglutamic dendrimers P-Glu$^4$ (128 carboxyls), C1-Glu$^3$ (64 carboxyls), C1-Glu$^4$ (128 carboxyls), and C2-Glu$^4$ (48 carboxyls). (G) Polyglutamic dendrons Glu$^3$ and Glu$^4$. (H) Size distributions of UCNP/dendrimers in aqueous solutions by DLS: UCNP/C1-Glu$^3$ (blue), UCNP/C1-Glu$^4$ (cyan), UCNP/C2-Glu$^4$ (red), UCNP/PAA (green), and UCNP/UCNP-BF$^4$—in DMF (black). (I) Vials with aqueous colloidal solutions of UCNP/PAA (Left) and UCNP/C1-Glu$^4$ (Right) containing equal amounts of the inorganic material (20 mg/mL). (J) Gel formed upon centrifugation of UCNP/P-Glu$^4$. A hand-held laser pointer (980 nm) generates a green luminescent trace (near the bottom of the tube). (K) A laser beam (980 nm) passing through a solution of UCNP/C1-Glu$^4$ is able to excite luminescence of UCNP/C2-Glu$^4$ in the vial behind. (L) The order of vials is changed. The beam now is strongly scattered by UCNP/C2-Glu$^4$, and no luminescence of UCNP/C1-Glu$^4$ can be seen. (M) TEM image of UCNP/PAA. (N) TEM image of UCNP/C1-Glu$^4$.

Surprisingly and unexpectedly, the inventors of the instant application have found that dendrimerizing the surface of nanoparticles (e.g., upconverting nanoparticles) by linking to a dendrite polymer or a hyperbranched polymer having a hydrophilic ionic group enhances the solubility of the nanoparticles, and as a result, provides fully water-soluble nanoparticles. In addition, the inventors of the instant application have surprisingly found that polyglutamic dendrimers having meso-3,5,-dialkoxyarylporphyrin "(P)" or C1 (see FIG. 8B herein) as the initial core fragment are able to engage the nanoparticle surface while remaining highly soluble. For example, polyglutamic dendrimer C1-Glu3 is unexpectedly soluble since it can engage ~18% of its carboxylates with the nanoparticle surface while the remaining ~72% are free to interact with the solvent (see Example 4 herein).

It will be appreciated that the term "nanoparticle" can encompass a particle having a diameter of from approximately 1 to approximately 500 nanometer (nm), having any size, shape or morphology, known to one of skilled in the art. It will also be appreciated that the the diameter of each nanoparticle can range between 1 nm and 500 nm, between 50 nm and 300 nm, or between 100 nm and 200 nm. In one embodiment, the diameter of each nanoparticle is about 500, 300, 200, 150, 100, 50 nm. In another embodiment, the diameter of each nanoparticle is 150 nm.

The surface dendrimerization to prepare water-soluble nanoparticles is applicable to any suitable nanoparticle known to one of skilled in the art. Examples of a nanoparticle include, but are not limited to, an up-converting nanoparticle, a down-converting nanoparticle, a metal nanoparticle, and an iron-oxide nanoparticle. Additional examples of a nanoparticle include, but are not limited to, a polymer, a macromolecule, a peptide, a protein, a polymersome, a multi-functional chelating agent, a nucleic acid, a polylysine, a dextran, or a combination thereof. In a particular embodiment, the nanoparticle is a lanthanide-based up-converting nanoparticle.

The methods for synthesizing nanoparticles are well known in the art. Any suitable method, known to one of skilled in the art, can be used. In one embodiment, upconverting nanoparticles (UCNPs) of the invention are synthesized by Ye et al., 2010, PNAS, vol. 107, pages 22430-22435. In some embodiments, nanoparticles are stabilized by coats of suitable ligands, such as, for example, oleic acid, polyethyleneamine, or even by secondary inorganic shells (e.g., mesoporous silica).

Dendritic polymers include, but are not limited to, symmetrical and unsymmetrical branching dendrimers, cascade molecules, arborols, and the like.

The term "dendrimer" is well known to any person of ordinary skill in the art. A dendrimer is a branched molecule. The dendrimer comprises a core or a focal point from which the branches of the dendrimer grow. A dendrimer may be characterized by number of "generations". The higher the generation, the more branched the dendrimer molecule is. Higher generations usually yield larger molecules.

In one embodiment, the diameter of spherical or pseudo-spherical dendrimers of the invention ranges between 0.2 nm and 20 nm. In one embodiment, the diameter of spherical or pseudo-spherical dendrimers of the invention ranges between 0.5 nm and 10 nm. In one embodiment, the diameter of spherical or pseudo-spherical dendrimers of the invention ranges between 1 nm and 4 nm. In one embodiment, for non-spherical dendrimers, the dimension ranges described herein above for diameter corresponds to the largest dimension describing the non-spherical dendrimer.

In one embodiment, the dendrimer is a polyglutamic dendrimer. In another embodiment, the dendrimer is a PAMAM dendrimer.

In one embodiment, the dendrimer is a fifth generation PAMAM dendrimer. In another embodiment, the dendrimer is between a second and tenth generation. The PAMAM to dendrimers disclosed herein are symmetric, in that the branch arms are of equal length. The branching occurs at the hydrogen atoms of a terminal —NH2 group on a preceding generation branch.

Even though not formed by regular sequential addition of branched layers, hyperbranched polymers, e.g., hyperbranched polyols, may be equivalent to a dendritic polymer where the branching pattern exhibits a degree of regularity approaching that of a dendrimer.

Topological polymers, with size and shape controlled domains, are dendrimers that are associated with each other (as an example covalently bridged or through other association) through their reactive terminal groups, which are referred to as "bridged dendrimers." When more than two dense dendrimers are associated together, they are referred to as "aggregates" or "dense star aggregates." Therefore, dendritic polymers include bridged dendrimers and dendrimer aggregates. Dendritic polymers encompass both generationally monodisperse and generationally polydisperse solutions of dendrimers. The dendrimers in a monodisperse solution are substantially all of the same generation, and hence of uniform size and shape. The dendrimers in a polydisperse solution comprise a distribution of different generation dendrimers.

Dendritic polymers also encompass surface modified dendrimers. For example, the surface of a dendrimer may be modified by the addition of an amino acid (e.g., lysine or arginine). As used herein, the term "generation" when referring to a dendrimer means the number of layers of repeating units that are added to the initiator core of the dendrimer. For example, a 1st generation dendrimer comprises an initiator core and one layer of the repeating unit, and a 2nd generation dendrimer comprises an initiator core and two layers of the repeating unit, etc. Sequential building of generations (i.e., generation number and the size and nature of the repeating units) determines the dimensions of the dendrimers and the nature of their interior. In one embodiment, the dendrimer is a fourth generation dendrimer. In another embodiment, the dendrimer is a third generation dendrimer.

The methods for synthesising dendritic polymers are well known in the art. Any suitable method, known to one of skilled in the art, can be used.

Methods for linking nanoparticles, for example, dendritic polymers to nanoparticles are well known to those of skill in the art, and include ligand exchange linkage, covalent linking, electrostatic-based linking, hydrogen bonds linking, coordinated-bond linking, linking based on hydrophobic interaction, or a combination thereof.

In one example, nanoparticles are first synthesized with capping ligands, for example, capping organic ligands (e.g., oleic acid ligands). These organic ligands are replaced by ligands possessing functional groups suitable for further modification or anions (e.g, BF4 ions).

In one embodiment, anions are displaced directly by dendritic polymers such as polyanionic dendrimers (e.g., polycarboxylate dendrimers).

In another embodiment, the ion modified nanoparicels can undergo secondary surface modification, for example $BF4^-$ modified upconverting nanoparticles can be modified by polymeric ligands such as polyacrylic acid (PAA) or polyethyleneamine (PEA), resulting in a large number of free carboxylic groups, as described herein. In some embodiments, the free functional groups of polymeric ligands not engaged in interactions with nanoparticles are covalently modified with polyanionic dendrimers (e.g., polycarboxylate dendrimers). The rationale for this two-step modification was two-fold: a) to establish principle feasibility of covalent modification of nanoparticles by dendrimers; and b) to test whether covalently-modified dendritic nanoparticles possess higher stability towards bases and acids.

In another embodiment, the ion modified nanoparticles can undergo secondary surface modification, for example $BE_4^-$ modified upconverting nanoparticles can be modified by polymeric dendrimers, as described herein.

In some embodiments, depending on the intended use, the peripheral groups (e.g. carboxyls) on the dendrimers are PEGylated by e.g methoxypolyethyleneglycolamine (PEG-$NH_2$), rendering neutral hydrophilic nanoparticles. This modification facilitates preventing interactions of nanoparticles with biological macromolecules. Alternatively, peripheral groups on the dendrimers, not engaged in bonding with nanoparticle surfaces can be used for linking nanoparticles to various targeting moieties, such as antibodies or cell-targetic peptides. Such linking can be achieved using conventional peptide chemistries or other standard methods, known to one of skilled in the art.

In some embodiments, the cross-linking agent that links a nanoparticle to a dendrite, hyperbranched polymer, or other molecule is, for example, a homobifunctional crosslinker, a heterobifunctional cross-linker, a linear polymer, a branched polymer, a nanoparticle, a nucleic acid, a peptide, a protein, or a combination thereof.

In one embodiment, the cross-linking agent is a thiol-ene chemistry linker. For example, thiol-reactive species can be made by coupling the dendrimer hydroxyl group to the isocyanate end of the bi-functional cross-linker, N-(p-maleimidophenyl)isocyanate, leaving a thiol-reactive maleimide for coupling to proteins. In one embodiment, a cross-linking agent is an agent that links one nanoparticle to one or more other nanoparticles; one nanoparticle to a paramagnetic ion (e.g., chelated gadolinium); one paramagnetic ion to another paramagnetic ion; or combinations thereof. In a particular embodiment, the cross-linking agent is a homobifunctional amine-reactive cross-linking agent, for example, NHS-PEG-NHS.

In another embodiment, nanoparticles are produced by crosslinking a source material (e.g., polycarboxylate dendrimers) in presence of a cross-linking agent known to one of skilled in the art. Uncrosslinked materials can be removed by multiple washes on centrifugal filter devices. Nanoparticles of the invention can also be produced by other methods known to one of skilled in the art. Examples of other methods include, but are not limited to, free radical polymerization and click chemistry.

The purified nanoparticles can be mixed with the ionic, chelated, or other forms of metals. The unreacted metals can be removed by multiple washes on centrifugal filter devices. The nanoparticles can be functionalized with a targeting agent. The labeled nanoparticles can be linked or coupled to a targeting ligand and/or a fluorescent probe (e.g., fluorescein isothiocyanate) using a method known to one of skilled in the art.

In some embodiments, the nanoparticles of the present invention may be used to detect the presence of a particular analyte, for example, pH, a protein, enzyme, polynucleotide, carbohydrate, antibody, or antigen. Molecular analytes include antibodies, antigens, polynucleotides, oligonucleotides, proteins, enzymes, polypeptides, polysaccharides, cofactors, receptors, ligands, and the like. The analyte may be a molecule found directly in a sample such as a body fluid from a host. The sample can be examined directly or may be pretreated to render the analyte more readily detectable. Furthermore, the analyte of interest may be determined by detecting a targeting ligand or agent probative of the analyte of interest such as a specific binding pair member complementary to the analyte of interest, whose presence will be detected only when the analyte of interest is present in a sample. Thus, the targeting ligand or agent probative of the analyte becomes the analyte that is detected in an assay.

The excitation energy transfer (EET) from the upconverted nanoparticles to auxiliary chromophores provides a convenient way of coupling upconversion to various functions performed by these chromophores. When the core of a dendrimer that is attached to the UCNP surface can perform simultaneously as an optical probe for a specific analyte (e.g., pH), UCNP-to-dendrimer EET can enable analyte sensing via upconverted luminescence, where UCNPs play the role of low-flux multiphoton antennae. This is in contrast to high-flux sensitization in dendritic systems with conventional antenna chromophores. Further polyglutamic porphyrin-dendrimers operate as efficient probes for pH in micro-heterogeneous systems and by exciting the UCNP/dendrimer compositions (e.g., UCNP/P-Glu$^4$ or UCNP/P-Glu$^3$) a ratiometric protonation curve can be constructed and the pH can be determined.

In one aspect, provided herein is a method of measuring the presence of an analyte in a sample, the method comprising contacting the sample with a composition comprising a plurality of nanoparticles, wherein the surface of each nanoparticle is dendrimerized with a plurality of dendrite polymers having a hydrophilic group or a hyperbranched polymer having a hydrophilic group, and wherein the dendrite polymers or hyperbranched polymers comprise an analyte-sensitive core that signals the presence of the analyte in said sample. In one embodiment, the core is a pH sensitive core or wherein said polyglutamic dendrimer comprises a pH sensitive core. In another embodiment, the pH sensitive core is meso-3,5-dialkoxyarylporhyrin (P). In another embodiment, the pH sensitive core is a fluorescent core.

It is to be understood that the analyte can include, but is not limited to, a hydrogen ion (FE) for measuring the pH of a sample, a biomarker for determining the presence of disease (e.g. cancer), or a drug.

In one embodiment, the sample is a biological sample. In another embodiment, the biological sample is present within a tissue interstitial space in a subject. In another embodiment, the analyte is hydrogen ion concencration [H+] and the methods provided herein enable the measurement of pH in tissue interstitial space in a subject. In another embodiment, the nanoparticle/dendrimer composition provided herein is administered to said subject by direct injection. In another embodiment, the method of measuring pH in interstitial space in a subject having a tumor. In another embodiment, injection in into said interstitial space near hypoxic tumors enables mapping of pH in hypoxic tumors.

In one embodiment, the method of measuring an analyte in a sample comprises visually measuring the emission spectra of said the nanoparticle/dendrimer composition. In another embodiment, the step of measuring the emission spectra of said composition further comprises rationing the visible bands of the nanoparticle. In a preferred embodiment, the nanoparticle is the upconverted nanoparticle (UCNP) described herein. In another embodiment, rationing visible UCNP bands enables the generation of a ratiometric protonation curve from which the pH can be calculated.

In one embodiment, fluorescence can be measured using methods known in the art which include but are not limited not, fluorescence microscopy, confocal fluorescence microscopy, high resolution two-photon laser scanning microscopy, and multi-photon miscroscopy.

In one embodiment, targeting ligands of the invention cover a range of suitable moieties. In another embodiment, a component may itself be used to generate a ligand by using the component to raise antibodies or to select aptamers that are specific binding partners for the component. In one embodiment, a suitable ligand may be known in the art. In other embodiments, antibodies can be raised to desired components by conventional techniques and can be provided, in certain embodiments, as monoclonal antibodies or fragments thereof, or as single chain antibodies produced recombinantly.

In one embodiment, the targeting ligand is coupled covalently to the nanoparticle. In another embodiment, the targeting ligand used in the methods described herein, is a small molecule, a peptide, a natural binding partner, another protein ligand, an antibody or their combinations. In one embodiment, the targeting ligand is specific for a marker of a pathology of interest.

In another embodiment, provided herein is a magnetic resonance imaging agent comprising the water-soluble nanoparticles described hereinabove. In one embodiment, the nanoparticles described hereinabove, is used in the methods described herein.

In one embodiment, provided herein is a magnetic resonance imaging (MRI) agent comprising, in another embodiment, a composition comprising the nanoparticles of any one of the embodiments described herein, linked to a ligand, wherein the ligand is specific for a pre-selected marker.

In one embodiment, the nanoclusters described hereinabove, are used in the methods of obtaining a pathology-specific magnetic resonance image (MRI) of a subject.

In one embodiment, the marker is a marker of a cancer, inflammation, autoimmune disease, cardiovascular disease, apoptosis or their combination in other discrete embodiments of the markers used in the methods described herein.

Accordingly, in one embodiment, provided herein is a method of obtaining a breast-cancer specific magnetic resonance image (MRI) of a subject, comprising administering to said subject a composition of the invention, wherein at least one of said nanoparticles is linked to an antibody, or a fragment thereof, specific against a carcinoembryonic antigen (CEA), thereby delivering a breast-cancer specific magnetic resonance image (MRI) of a subject.

The paramagnetic metals useful in the MRI contrast agents described herein include rare earth metals, typically, lanthanum, ytterbium, gadolinium, europium, and the like. Iron ions and manganese ions may also be used. Also included in the surface of the nanoparticle, in some embodiments described herein, are biologically active agents. These biologically active agents can be of a wide variety, including proteins, nucleic acids, and the like. Thus, included among suitable pharmaceuticals are antineoplastic agents, hormones, analgesics, anesthetics, neuromuscular blockers, antimicrobials or antiparasitic agents, antiviral agents, interferons, antidiabetics, antihistamines, antitussives, anticoagulants, and the like.

In one embodiment, the inclusion of a chelating agent containing a paramagnetic ion is useful as a magnetic resonance imaging contrast agent. The inclusion of biologically active materials makes them useful as drug delivery systems. The inclusion of radionuclides makes them useful either as therapeutics for radiation treatment or as diagnostics for imaging or both. A multiplicity of such activities may be included; thus, images can be obtained of targeted tissues at the same time active substances are delivered to them. In another embodiment, a radionuclide may be coupled to the nanoparticle. Means to attach various radioligands to the nanoparticles described herein are well known in the art.

In one embodiment, the water-soluble nanoparticle composition of the invention can be combined with one or more other compositions. In one embodiment, the water-soluble nanoparticle composition of the invention can be combined with another composition comprising a liposome. In another embodiment, the water-soluble nanoparticle composition of the invention can be combined with another composition comprising a carbohydrate. In another embodiment, the water-soluble nanoparticle composition of the invention can be combined with another composition comprising a suitable multivalent agent known to one of skilled in the art. In another embodiment, the water-soluble nanoparticle composition of the invention can be combined with another composition comprising a drug. In another embodiment, the water-soluble nanoparticle composition of the invention can be combined with another composition comprising a contrast agent.

In some embodiments, the composition can be formulated in pharmaceutical compositions for in vivo administration, preferably to a mammal, more preferably to a human. These compositions can comprise, in addition to one or more of the compounds of the invention, a pharmaceutically acceptable excipient, carrier, buffer, stabiliser or other materials well known to those skilled in the art. Such materials are preferably non-toxic and may not interfere with the function of the components in the composition. The precise nature of the carrier or other material can depend on the route of administration, e.g. intravenous, cutaneous or subcutaneous, nasal, intramuscular, intraperitoneal routes.

The mode of administration, the dosage and frequency of dosage is governed by the mode of administration and dosage considerations conventionally employed with the contrast agent. Typically, these agents are administered by intravenous injection immediately prior to subjecting the patient to a magnetic resonance imaging procedure. Other routes of administration may be utilized as dictated by medical and pharmacological practice related to the desired use of the particular contrast agent employed. It will be understood that the specific dose level for any particular patient will depend upon a variety of factors including the specific agent employed, the age, body weight, general health, sex, diet, time of administration, route of administration and rate of excretion. Examples of the techniques and protocols mentioned above can be found in Remington's Pharmaceutical Sciences, 16th edition, Osol, A. (ed), 1980.

The term "subject," as used herein, includes any human or non-human animal. The term "non-human animal" includes all vertebrates, e.g., mammals and non-mammals, such as non-human primates, sheep, dog, cow, chickens, amphibians, reptiles, etc.

Any patent, patent application publication, or scientific publication cited herein is incorporated by reference herein in their entirety.

The following examples are presented in order to more fully illustrate the preferred embodiments of the invention. They should in no way be construed, however, as limiting the broad scope of the invention.

EXAMPLES

Synthesis of Dendrimers

Materials and Methods

All solvents and reagents were purchased from commercial sources and used as received.

Figure 1:
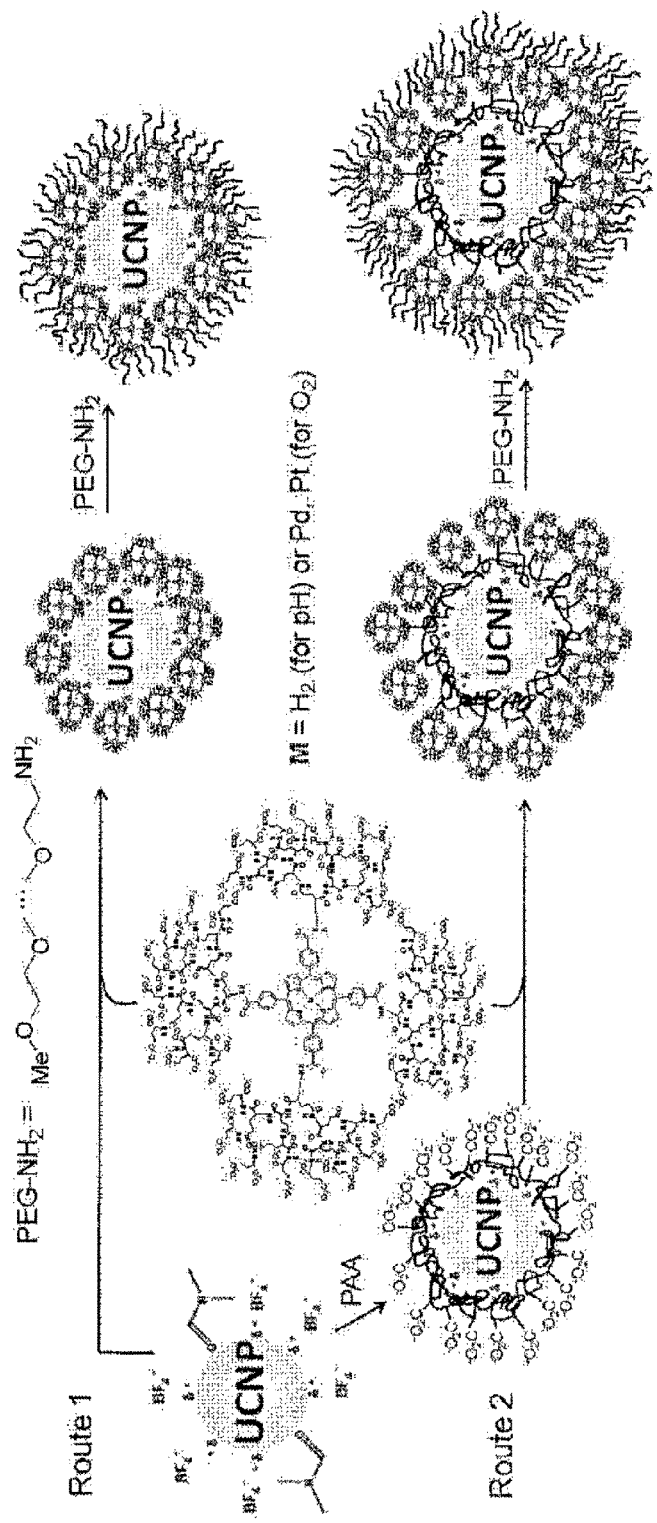
FIG. 1 shows the scheme of producing water-soluble up-converting nanoparticles (UCNPs). The scheme depicts two modification methods, which result in functionally identical, but structurally slightly different dendritic UCNPs.
Figure 2:
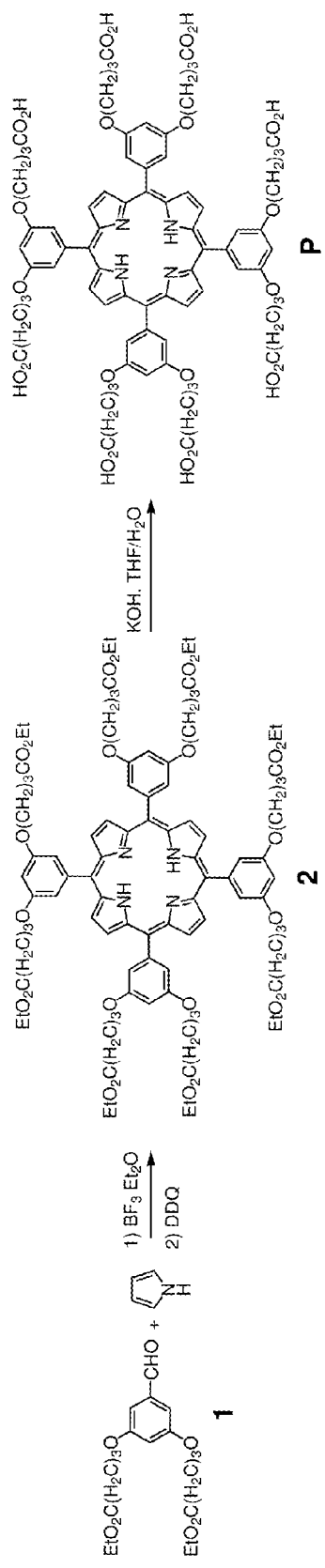
FIG. 2 shows core P synthesis in the process of dendrimer synthesis.

1) Core P (Scheme 1; FIG. 2)

tetra-meso-[3,5-Bis(3-carboxypropyloxy)phenyl]-porphyrin (P)

To a solution of 3,5-bis(3-ethoxycarbonylpropyloxy)benzaldehyde (1) (1), (0.366 g, 1 mmol) and pyrrole (0.07 ml, 1 mmol) in $CH_2Cl_2$ (100 ml) $BF_3.Et_2O$ (0.025 ml, 0.2 mmol) was added, and the reaction mixture was stirred in the dark under Ar for 2 h. DDQ (0.227 g, 1 mmol) was added, and the mixture stirred overnight at r.t. in the dark. The solvent was evaporated to dryness, and the product was purified by column chromatography ($SiO_2$, eluent $CH_2Cl_2$/THF, 20:1) to give porphyrin octaethyl ester 2. Yield: 90 mg, 22%.

Octaethyl ester 2 (90 mg, 0.054 mmol) was dissolved in THF (15 ml), KOH (0.152 g, 2.7 mmol) and $H_2O$ (0.15 ml) were added, and the reaction mixture was stirred overnight at r.t. The formed precipitate was isolated by centrifugation, dissolved in aq. KOH (0.1 M, 20 ml) and stirred for additional 2 h at r. t. The solution was cooled to 0° C. on an ice bath, acidified with 10% HCl to pH 4-5. The formed precipitate was isolated by centrifugation, washed with water 3 times and dried in vacuum, giving the target product P as a green powder. Yield: 0.065 g (83%). MALDI-TOF (m/z): calc. for $C_{76}H_{78}N_4O_{24}$: 1430.5, found 1431.8 $[M+H]^+$. NMR $^1H$ (DMSO-$d_6$), δ, ppm: 2.14 (16H, dddd, $^3J_1=^3J_2=6.7$ $^3J_3=^3J_4=6.5$ Hz, —$CH_2$—), 2.53 (16H, t, $^3J=7.1$ Hz, —$CH_2C(O)$—), 4.34 (16H, t, broad, $^3J=5.8$ Hz, —$OCH_2$—), 7.22 (4H, s, Ar) 7.86 (8H, s, Pyr), 8.85 (8H, s, Ar).

Figure 3:
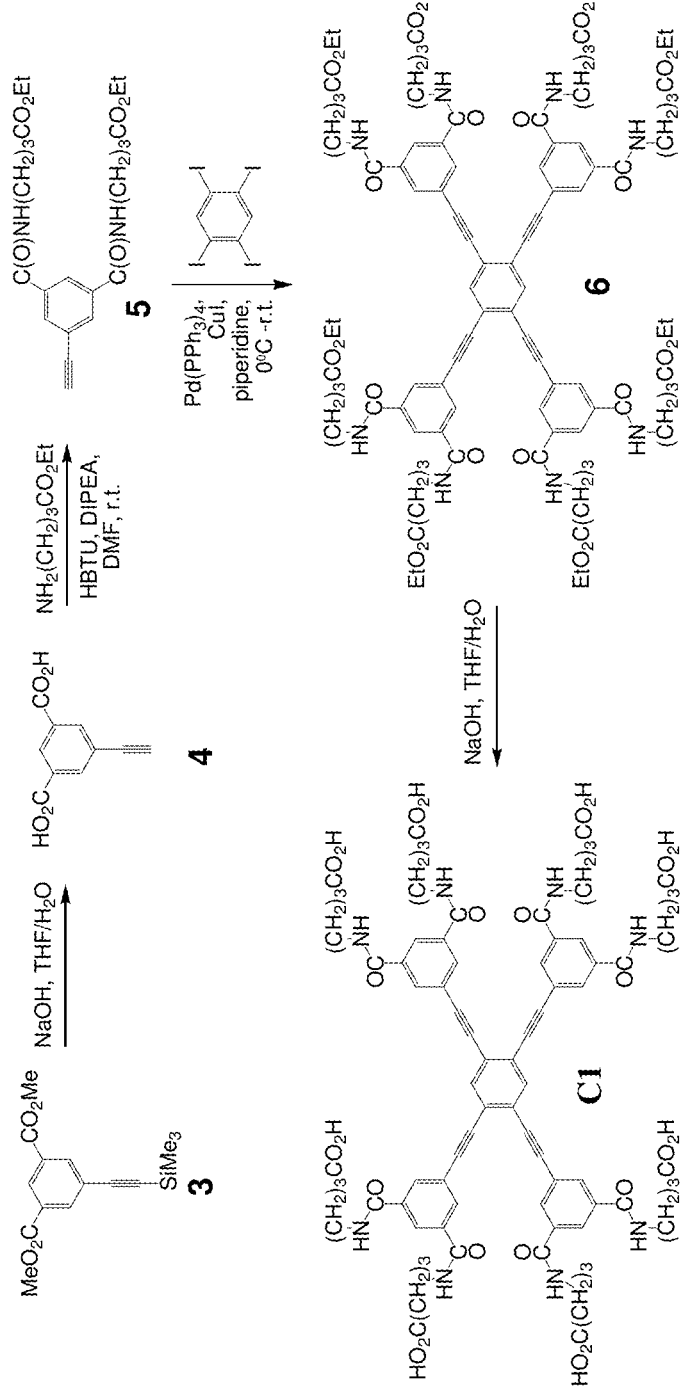
FIG. 3 shows core C1 synthesis in the process of dendrimer synthesis.

2) Core C1 (Scheme 2; FIG. 3)

Dimethyl-5-(trimethylsilylethynyl)isophthaloate (3) was synthesized.

5-Ethynylisophthalic acid (4)

5-Ethynylisophthalic acid was prepared in one step by reacting dimethyl-5-(trimethylsilylethynyl)isophthaloate (3) (0.7 g, 3.2 mmol) with NaOH (1.412 g, 35.3 mmol) in THF (20 ml) at r. t. for ~4 h. The precipitate formed was centrifuged down, dissolved in aq. NaOH (0.1 M, 50 ml) and stirred for 2 h at room temperature. The reaction mixture was cooled to 0° C. on an ice bath, acidified with 10% HCl to pH~1-2. The precipitate formed was isolated by centrifugation, washed twice with water and dried, giving the target compound as a powder. Yield: 0.47 g, 77%.

Diethyl 4,4'-[(5-ethynyl-1,3-phenylene)bis(carbonylimino)]dibutanoate (5)

To a solution of 5-ethynylisophthalic acid (4) (0.37 g, 1.95 mmol) in dry DMF (20 ml), HBTU (2 g, 5.28 mmol) was added in one portion. After stirring for 10 min at r. t., the mixture of ethyl 4-aminobutyrate hydrochloride (1 g, 5.97 mmol) and DIPEA (2 ml, 11.5 mmol) in dry DMF (10 ml) was added, and the reaction mixture was stirred overnight at r. t. The reaction mixture was poured into ice-cold water (200 ml), and a few drops of conc. HCl were added. The formed precipitate was centrifuged, washed 3 times with water and dried in vacuum. The product was purified by column chromatography ($SiO_2$, eluent $CH_2Cl_2$/THF, gradient from 100:0 to 80:20) to yield the target compound as a yellowish solid. Yield: 0.6 g, 74%. NMR $^1$H (DMSO-$d_6$), δ, ppm: 1.16 (6H, t, $^3J$=7.0 Hz, —OCH$_2$C$\underline{H}_3$), 1.77 (4H, dddd, $^3J_1$=$^3J_2$=7.0, $^3J_3$=$^3J_4$=7.3 Hz, —C$\underline{H}_2$—), 2.35 (4H, t, $^3J$=7.3 Hz, —C$\underline{H}_2$C(O)—), 3.24-3.31 (4H, m, broad, —NHC$\underline{H}_2$—), 4.03 (4H, q, $^3J$=7.0 Hz, —OC$\underline{H}_2$CH$_3$), 4.37 (1H, s, —C≡$\underline{H}$), 8.05 (2H, d, $^4J$=1.7 Hz, to Ar), 8.30 (1H, t, $^4J$=1.7 Hz, Ar), 8.60 (2H, t, $^3J$=5.5 Hz, —N$\underline{H}$—).

4,4',4'',4''',4'''',4''''',4'''''',4'''''''(4-tetrayltetrakis[ethyn-1,2-diylbenzene-5,1,3-triylbis(carbonylimino)]))octabutanoic acid (C1)

1,2,4,5-Tetraiodobenzene (0.165 g, 0.284 mmol) was dissolved in piperidine (3 ml), and the solution was bubbled with Ar under stirring over 30 min period. The catalyst, Pd(PPh$_3$)$_4$ (0.131 g, 0.114 mmol, 40 mol %), was added, and the reaction mixture was bubbled with Ar for additional 15 min 5 (0.568 g, 1.36 mmol) was dissolved in piperidine (10 ml) under Ar, and the solution was cooled to 0° C. on an ice bath. The mixture of tetraiodobenzene and the catalyst was rapidly added to the solution of 5, followed by addition of CuI (0.011 g, 0.057 mmol, 20 mol %). The reaction mixture was stirred at r. t. overnight under Ar, after which it was quenched with saturated aqueous solution of NH$_4$Cl (30 ml). The products were extracted with CH$_2$Cl$_2$ (3×30 ml), and the combined organic layers were dried over Na$_2$SO$_4$. The solvent was evaporated, and the product was purified by column chromatography (SiO$_2$, CH$_2$Cl$_2$ then CH$_2$Cl$_2$/THF, 3:1, and finally, CH$_2$Cl$_2$/MeOH, 30:1) to give 6 as a light-yellow solid. Yield: 0.150 g (30%).

6 (0.15 g, 0.086 mmol) was dissolved in THF (15 ml), NaOH (0.275 g, 6.9 mmol) and water (0.15 ml) were added, and the reaction mixture was stirred overnight at r. t. The formed precipitate was isolated by centrifugation, dissolved in aq. NaOH (0.1 M, 20 ml) and stirred for additional 2 h at r. t. The solution was cooled to 0° C. on an ice bath, acidified with 10% aq. HCl to pH 4-5. The precipitate formed was collected by centrifugation and washed with water 3 times, yielding bright yellow powder. Yield: 0.12 g, 92%. MALDI-TOF (m/z): calc. for C$_{78}$H$_{78}$N$_8$O$_{24}$: 1510.5, found 1533.7 [M+Na]$^+$. NMR $^1$H (DMSO-$d_6$), δ, ppm: 1.73 (16H, dddd, $^3J_1$=$^3J_2$=7.0 $^3J_3$=$^3J_4$=7.3 Hz, —C$\underline{H}_2$—), 2.26 (16H, t, $^3J$=7.3 Hz, —C$\underline{H}_2$C(O)—), 3.22-3.31 (16H, m, broad, —NHC$\underline{H}_2$—), 4.03 (16H, q, $^3J$=7.0 Hz, —OC$\underline{H}_2$CH$_3$), 8.09 (2H, s, Ar), 8.15-8.19 (8H, d, $^4J$=1.5 Hz, Ar), 8.32-8.36 (4H, t, $^4J$=1.5 Hz, Ar), 8.67 (2H, t, $^3J$=5.5 Hz, —N$\underline{H}$—), 12.06 (8H, broad, —C(O)O$\underline{H}$).

Figure 4:
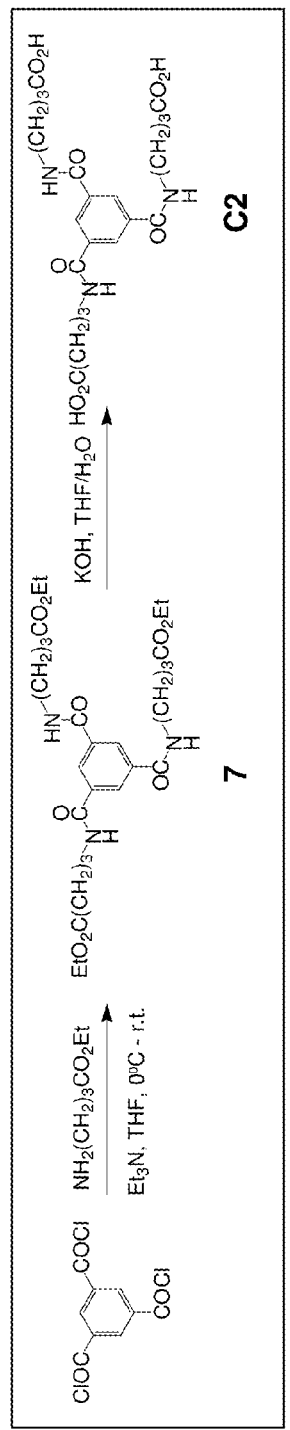
FIG. 4 shows core C2 synthesis in the process of dendrimer synthesis.

3) Core C2 (scheme 3; FIG. 4)

Triethyl 4,4',4''-[benzene-1,3,5-triyltris(carbonylimino)]tributanoate (7)

To a solution of ethyl 4-aminobutyrate hydrochloride (1.983 g, 11.3 mmol) in THF (40 ml), a mixture of 1,3,5-benzenetricarbonyl trichloride (1.0 g, 3.8 mmol) and triethylamine (3.5 ml, 25 mmol) was added dropwise at 0° C. The reaction mixture was stirred at r. t. overnight, then poured into water (120 ml), extracted with Et$_2$O (4×40 ml) and dried over Na$_2$SO$_4$. The solvent was evaporated, and the product was purified by column chromatography (SiO$_2$, CH$_2$Cl$_2$/EtOAc/MeOH, 45:45:10) to give the title compound as a white solid. Yield: 1.65 g, 79%. MALDI-TOF (m/z): calc. for C$_{27}$H$_{39}$N$_3$O$_9$: 549.6, found 550.5 [M+H]$^+$, 572.5 [M+Na]$^+$, 588.5 [M+K]$^+$. NMR $^1$H (DMSO-$d_6$), δ, ppm: 1.16 (9H, t, $^3J$=7.0, Hz, —OCH$_2$C$\underline{H}_3$), 1.79 (6H, dddd, $^3J_1$=$^3J_2$=$^3J_3$=3J$_4$=7.3 Hz, —C$\underline{H}_2$—), 2.35 (6H, t, $^3J$=7.3 Hz, —CH$_2$C(O)—), 3.27-3.33 (6H, m, broad, —NHC$\underline{H}_2$—), 4.04 (6H, q, $^3J$=7.0 Hz, —OC$\underline{H}_2$CH$_3$), 8.37 (3H, s, Ar), 8.71 (3H, t, $^3J$=5.5 Hz, —N$\underline{H}$—).

4,4',4''-[Benzene-1,3,5-triyltris(carbonylimino)]tributanoic acid (C2)

7 (1.5 g, 2.73 mmol) was dissolved in THF (50 ml). KOH (2.3 g, 41 mmol) and water (0.5 ml) were added, and the mixture was stirred overnight at r. t. The formed precipitate was isolated by centrifugation, dissolved in KOH aq. (0.1M, 50 ml) and stirred for additional 2 h at r. t. The reaction mixture was cooled to 0° C. on an ice bath, acidified with 10% HCl to pH 4-5. The formed precipitate was collected by centrifugation, washed with water 3 times and dried in vacuum. Yield: 0.6 g, 50%. The obtained compound was used in the following coupling reactions without further purification.

Figure 5:
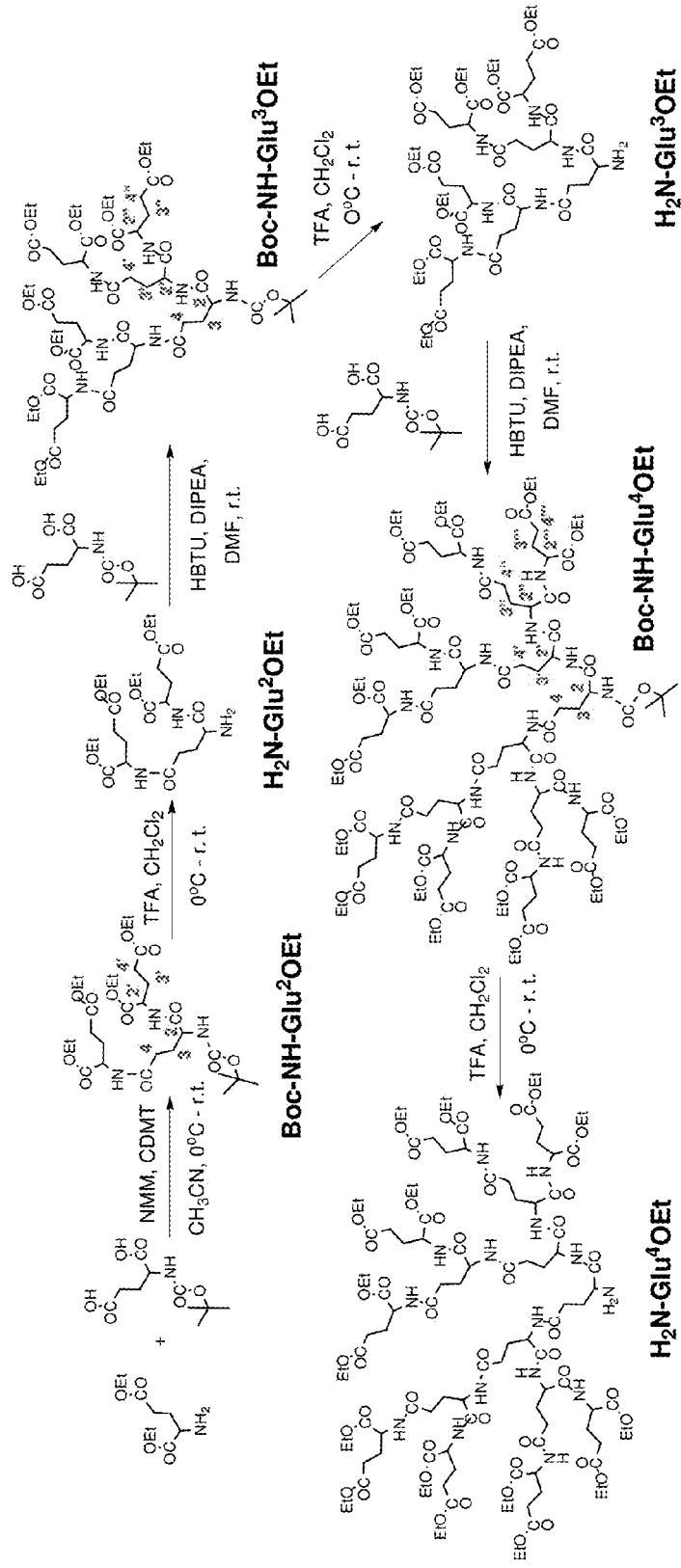
FIG. 5 shows synthesis of polyglutamic dendrons.

B) Polyglutamic Dendrons (Scheme 4; FIG. 5)

In Scheme 4 and description below, dendrons and dendrimers are designated using abbreviations developed previously.

Boc-HN-Glu$^2$OEt.

To a mixture of N-(tert-butoxycarbonyl)-L-glutamic acid (6 g, 24.3 mmol), L-glutamic acid diethyl ester hydrochloride (11.64 g, 48.5 mmol) and 2-chloro-4,6-dimethoxy-1,3,5-triazine (CDMT), (9.38 g, 53.4 mmol) in dry acetonitrile (420 ml), kept on an ice-cold bath, N-methylmorpholine (NMM), (10.67 ml, 97 mmol) was added drop-wise over 10 min period. The mixture was stirred overnight at r. t. The obtained mixture was concentrated in vacuum to ~80 ml, 300 ml of water was added, and the resulting mixture was stirred for 2-3 h at r. t. until a white precipitate formed. The precipitate was collected by filtration, washed with water (4×100 ml) and dried in vacuum to give pure title compound. Yield: 11.6 g, 77%. NMR $^1$H (DMSO-$d_6$, 80° C.), δ, ppm: 1.15-1.20 (12H, m, —C(O)OCH$_2$C$\underline{H}_3$), 1.38 (9H, s, —C(O)OC(C$\underline{H}_3$)$_3$), 1.66-1.77 (1H, m, (3)-C$\underline{H}_2$—), 1.79-1.93 (3H, m, (3,3',3')—C$\underline{H}_2$—), 1.93-2.07 (2H, m, (3',3')-C$\underline{H}_2$—), 2.14-2.23 (2H, m, (4)-C$\underline{H}_2$—), 2.30-2.39 (4H, m, (4',4')-C$\underline{H}_2$—), 3.88-3.97 (1H, m, (2)-C$\underline{H}$(NH)—), 4.01-4.12 (8H, m, —C(O)OC$\underline{H}_2$CH$_3$), 4.21-4.33 (2H, m, (2',2')-C$\underline{H}$(NH)—), 6.60-6.70 (1H, m, broad, —N$\underline{H}$—), 7.96-8.04 (2H, m, —N$\underline{H}$—).

H$_2$N-Glu$^2$OEt.

Boc-N-Glu$^2$OEt (10 g, 16.2 mmol) was dissolved in CH$_2$Cl$_2$ (50 ml). The solution was cooled to 0° C. on an ice bath, trifluoroacetic acid (50 ml) was added slowly, and the mixture was allowed to react overnight under stirring, after which the solution was concentrated and dried under vacuum. The residue was dissolved in CH$_2$Cl$_2$ (350 ml), washed m with water (250 ml), then with aq. NaHCO$_3$ (10%, 2×200 ml), finally with brine (250 ml) and dried over Na$_2$SO$_4$. The solvent was evaporated to give the title compound as a light-yellow solid (6.95 g, 83%). H$_2$N-Glu$^2$OEt was used in the following coupling reactions without further purification.

Boc-NH-Glu$^3$OEt.

To a solution of N-(tert-butoxycarbonyl)-L-glutamic acid (0.86 g, 3.48 mmol) in dry DMF (20 ml), HBTU (2.9 g, 7.66 mmol) was added, and the mixture was stirred for 10 min at r. t. A solution of H$_2$N-Glu$^2$OEt (3.6 g, 7.0 mmol) in dry DMF (25 ml) was rapidly added to the mixture, followed by addition of DIPEA (2.5 ml, 13.9 mmol). The reaction mixture was stirred overnight at r. t. and poured into water (250 ml). The white precipitate formed was collected by centrifugation, washed with water (2×100 ml) and dried in vacuum to the title compound as a white solid. Yield: 4.2 g, 97%. MALDI-TOF (m/z): calc. for C$_{57}$H$_{93}$N$_7$O$_{23}$: 1244.37, found 1268.159 [M+Na]$^+$. NMR $^1$H (DMSO-d$_6$, 80° C.), δ, ppm: 1.14-1.20 (24H, m, —C(O)OCH$_2$CH$_3$), 1.37 (9H, s, —C(O)OC(CH$_3$)$_3$), 1.69-2.05 (14H, m, (3,3',3")-CH$_2$—), 2.14-2.23 (6H, m, (4,4')-CH$_2$—), 2.31-2.38 (8H, m, (4")-CH$_2$—), 3.85-3.92 (1H, m, (2)-CH(NH)—), 4.01-4.12 (16H, m, —C(O)OCH$_2$CH$_3$), 4.22-4.34 (6H, m, (2',2")-CH(NH)—), 6.66-6.82 (1H, m, broad, —NH—), 7.74-7.86 (2H, m, —NH—), 7.98-8.02 (2H, m, —NH—), 8.15 (1H, d, $^3$J=7.8 Hz, —NH—), 8.19-8.25 (1H, m, broad —NH—).

H$_2$N-Glu$^3$OEt.

The synthesis of H$_2$N-Glu$^3$OEt from Boc-NH-Glu$^3$OEt (4.2 g, 3.38 mmol) followed the procedure described above for Gen 2 dendron H$_2$N-Glu$^2$OEt. The title compound was isolated as a light-yellow solid. Yield: 3.79 g, 98%. It was used in the following coupling reactions without further purification.

Boc-NH-Glu$^4$OEt.

To a solution of N-(tert-butoxycarbonyl)-L-glutamic acid (0.37 g, 1.5 mmol) in dry DMF (10 ml), HBTU (1.26 g, 3.3 mmol) was added, and the mixture stirred for 10 min at r. t. A solution of NH$_2$Glu$^3$OEt (3.79 g, 3.3 mmol) in dry DMF (25 ml) was rapidly added to the mixture, followed by addition of DIPEA (1.1 ml, 6.0 mmol). The reaction mixture was stirred overnight at r. t. and poured into water (150 ml). The white precipitate formed was collected by centrifugation, washed with water (2×80 ml) and dried in vacuum to give the title compound as a white solid. Yield: 2.9 g, 77%. MALDI-TOF (m/z): calc. for C$_{112}$H$_{179}$N$_{15}$O$_{48}$: 2503.7, found 2526.1 [M+Na]$^+$, 2404.1 [M-Boc]$^+$. NMR $^1$H (DMSO-d$_6$, 80° C.), δ, ppm: 1.13-1.21 (48H, m, —C(O)OCH$_2$CH$_3$), 1.38 (9H, s, —C(O)OC(CH$_3$)$_3$), 1.71-2.05 (30H, m, (3,3',3''',3''')-CH$_2$—), 2.15-2.25 (14H, m, (4,4',4''')-CH$_2$—), 2.31-2.39 (16H, m, (4''')-CH$_2$—), 3.87-3.94 (1H, m, (2)-CH(NH)—), 4.02-4.13 (32H, m, —C(O)OCH$_2$CH$_3$), 4.21-4.34 (14H, m, (2',2'',2''')-CH(NH)—), 6.58-6.66 (1H, m, broad, —NH—), 7.64-7.78 (4H, m, —NH—), 7.86-7.94 (5H, m, —NH—), 8.04 (1H, d, $^3$J=7.8 Hz, —NH—), 8.06-8.10 (4H, m, broad —NH—).

H$_2$N-Glu$^4$OEt.

The synthesis of H$_2$N-Glu$^4$OEt from Boc-NH-Glu$^4$OEt (2.9 g, 1.16 mmol) followed the procedure described for the Gen 2 and Gen 3 dendrons above. The title compound was isolated as a light-yellow solid. Yield: 2.4 g, 86%. H$_2$N-Glu$^4$OEt was used in the following coupling reactions without further purification.

Figure 6:
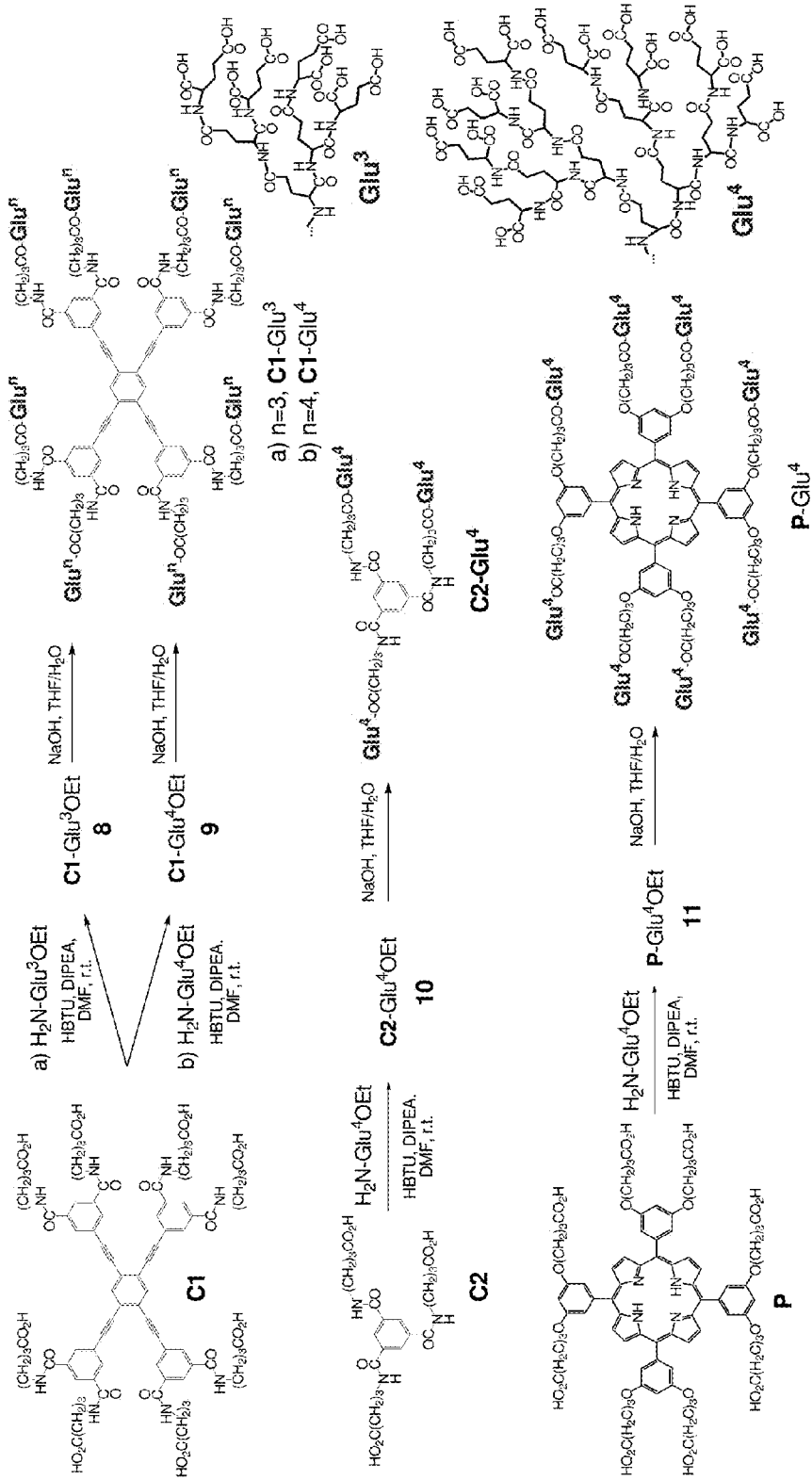
FIG. 6 shows synthesis of dendrimers.

C) Dendrimers (Scheme 5; FIG. 6)

C1-Glu$^3$OEt (8).

HBTU (0.082 g, 0.22 mmol) was added to a solution of C1 (0.0325 g, 0.022 mmol) in dry DMF (5 ml), and the resulted mixture was stirred for 10 min at r. t. A solution of H$_2$N-Glu$^3$OEt (0.1254 g, 0.175 mmol, 8.1 eq) in dry DMF (10 ml) was rapidly added to the mixture, followed by addition of DIPEA (0.15 ml, 0.86 mmol). The mixture was stirred at r. t. for 48 h, while monitored by MALDI-TOF analysis. After the reaction completion, the mixture was poured into water (150 ml). The while precipitate formed was collected by centrifugation, washed with water (3×100 ml) and dried in vacuum to give the title compound as a light-yellow solid (0.174 g, 87%). Yield: 0.174 g, 87%. MALDI-TOF (m/z): calc. for C$_{486}$H$_{726}$N$_{64}$O$_{192}$: 10526.0, found 10565.0 [M+K]$^+$. NMR $^1$H (DMSO-d$_6$, 80° C.), δ, ppm: 1.12-1.20 (192H, m, —C(O)OCH$_2$CH$_3$), 1.69-2.05 (128H, m, —CH$_2$—, (3,3',3")-CH$_2$—), 2.15-2.25 (64H, m, —CH$_2$C(O)—, (4,4')-CH$_2$—), 2.29-2.38 (64H, m, (4")-CH$_2$—), 3.23-3.32 (16H, m, broad, —NHCH$_2$—), 3.99-4.11 (128H, m, —C(O)OCH$_2$CH$_3$), 4.16-4.34 (56H, m, (2,2',2")-CH(NH)—), 7.76-7.84 (16H, m, broad, —NH—), 7.87-7.97 (24H, m, broad, —NH—), 8.00 (2H, s, Ar), 8.06-8.12 (16H, m, broad, —NH—), 8.12-8.15 (8H, m, broad, Ar), 8.31-8.36 (4H, m, broad, Ar), 8.40-8.49 (8H, m, broad Ar—NH—).

C1-Glu$^3$.

8 (0.15 g, 0.014 mmol) was dissolved in THF (50 ml). NaOH (0.37 g, 9.3 mmol) and water (0.2 ml) were added to the mixture, and it was let under stirring overnight at r. t. The precipitate formed was collected by centrifugation, re-dissolved in aq. NaOH (0.1 M, 15 ml) and stirred for additional 6 h at r. t. The solution was cooled to 0° C. on an ice bath, acidified with 10% HCl to pH 7, and the residual THF was removed under vacuum. The resulting solution was passed through a Millipore filter (0.45 μm av. pore diameter), the pH was adjusted to 7.0, and the solution was purified by dialysis for 3 days (12 kDa cut-off membrane). The purified solution was lyophilized to give the title dendrimer (sodium salt) as a bright-yellow solid. Yield: 0.12 g, 83%.

C1-Glu$^4$OEt (9).

To a solution of C1 (0.045 g, 0.03 mmol) in dry DMF (5 ml), HBTU (0.113 g, 0.298 mmol) was added, and the resulted mixture was stirred for 10 min at r. t. A solution of H$_2$NGlu$^4$OEt (0.584 g, 0.24 mmol, 8.1 eq) in dry DMF (25 ml) was rapidly added to the mixture, followed by addition of DIPEA (0.21 ml, 1.19 mmol). The reaction mixture was stirred at r. t. for 3 days, while being monitored by MALDI-TOF analysis. After reaction completion, the mixture was poured into water (300 ml). The precipitate formed was collected by centrifugation, washed with water (3×100 ml), and dried in vacuum to give the title compound as light-yellow solid. Yield: 0.537 g, 87%. MALDI-TOF (m/z): calc. for C$_{934}$H$_{1430}$N$_{128}$O$_{384}$: 20574.0, found range ~13500-21000 with maxima at 18228.5 [C1-Glu$^4$OEt+K]$^+$, and 15912.1. NMR $^1$H (DMSO-d$_6$, 80° C.), δ, ppm: 1.12-1.20 (384H, m, —C(O)OCH$_2$CH$_3$), 1.68-2.06 (256H, m, —CH$_2$—, (3,3',3''',3''')-CH$_2$—), 2.14-2.27 (128H, m, —CH$_2$C(O)—, (4,4',4''')-CH$_2$—), 2.29-2.38 (128H, m, (4''')-CH$_2$—), 3.23-3.31 (16H, m, broad, —NHCH$_2$—), 4.00-4.12 (256H, m, —C(O)OCH$_2$CH$_3$), 4.17-4.34 (120H, m, (2,2',2'',2''')-CH(NH)—), 7.71-8.19 (130H, broad, Ar, —NH—), 8.29-8.37 (4H, m, broad, Ar), 8.38-8.53 (8H, m, broad Ar—NH—).

C1-Glu$^4$.

9 (0.5 g, 0.024 mmol) was dissolved in THF (100 ml). NaOH (1.2 g, 30 mmol) and water (0.5 ml) were added to the solution, and the mixture was allowed to react overnight under stirring at r. t. The precipitate formed was collected by centrifugation, dissolved in aq. NaOH (0.1 M, 20 ml) and stirred for additional 6 h at r. t. The following workup and purification followed those for C1-Glu$^3$. C1-Glu$^4$ was isolated as a bright-yellow solid (sodium salt). Yield: 0.42 g, 87%.

C2-Glu$^4$OEt (10).

To a solution of C2 (0.03 g, 0.065 mmol) in dry DMF (2 ml), HBTU (0.082 g, 0.216 mmol) was added, and the reaction mixture was stirred for 10 min at r. t. A solution of H$_2$NGlu$^4$OEt (0.5 g, 0.208 mmol, 3.2 eq) in DMF (15 ml) was rapidly added to the mixture, followed by addition of DIPEA (0.2 ml, 1.25 mmol). The mixture was stirred for 48 h at r. t., monitored by MALDI-TOF analysis. After reaction completion, the mixture was poured into water (200 ml). The precipitate formed was collected by centrifugation, washed with water 3 times and dried in vacuum to give the title compound as a white solid. Yield: 0.428 g, 87%. MALDI-TOF (m/z): calc. for C$_{342}$H$_{534}$N$_{48}$O$_{114}$: 7614.0, found 7652.9 [M+K]$^+$. NMR $^1$H (DMSO-d$_6$, 80° C.), δ, ppm: 1.13-1.21 (144H, m, —C(O)OCH$_2$C$\underline{H}_3$), 1.68-2.06 (96H, m, —C$\underline{H}_2$—, (3,3',3",3'")-C$\underline{H}_2$—), 2.13-2.30 (48H, m, —C$\underline{H}_2$C(O)—, (4,4',4")-C$\underline{H}_{27}$), 2.30-2.39 (48H, m, (4'")-C$\underline{H}_2$—), 3.24-3.36 (6H, m, broad, —NHC$\underline{H}_2$—), 4.00-4.12 (96H, m, —C(O)OC$\underline{H}_2$CH$_3$), 4.18-4.34 (45H, m, (2,2', 2",2'")-C$\underline{H}$(NH)—), 7.73-8.17 (45H, m, broad, —N$\underline{H}$—), 8.37 (3H, s, Ar), 8.42-8.49 (3H, m, broad Ar—N$\underline{H}$—).

C2-Glu$^4$.

10 (0.425 g, 0.056 mmol) was dissolved in THF (100 ml), NaOH (1.1 g, 27.5 mmol) and water (0.5 ml) were added to the solution, and it was left to react overnight under stirring at r. t. The precipitate formed was collected by centrifugation, dissolved in NaOH aq. (0.1 M, 20 ml) and stirred for additional 6 h at r. t. The following work up and purification followed that for C1-Glu$^3$ and C1-Glu$^4$. The title dendrimer (sodium salt) was isolated as an off-white solid. Yield: 0.37 g, 91%.

P-Glu$^4$OEt (11).

To a solution of P (0.0273 g, 0.019 mmol) in dry DMF (5 ml) HBTU (0.075 g, 0.19 mmol) was added, and the reaction mixture was stirred for 10 min at r. t. A solution of NH$_2$Glu$^4$OEt (0.3718 g, 0.155 mmol, 8.1 eq) in DMF (15 ml) was rapidly added to the mixture, followed by the addition of DIPEA (0.15 ml, 0.76 mmol). The mixture was stirred at r. t. for 3 days, while being monitored by MALDI-TOF analysis. After reaction completion, the mixture was poured into water (300 ml). The precipitate formed was collected by centrifugation, washed with water (3×100 ml), and dried in vacuum to give the title compound as green solid. Yield: 0.429 g, 87%. MALDI-TOF (m/z): calc. for C$_{932}$H$_{1430}$N$_{124}$O$_{384}$: 20494.0, found 20532.6 [M+K]$^+$, fragment ions: 19468.5, 18212, 17110, 15835.5, 14778. NMR $^1$H (DMSO-d$_6$, 80° C.), δ, ppm: 1.09-1.20 (384H, m, —C(O)OCH$_2$C$\underline{H}_3$), 1.71-2.05 (256H, m, —C$\underline{H}_2$—, (3,3',3", 3'")-C$\underline{H}_2$—), 2.15-2.25 (112H, m, (4,4',4")-C$\underline{H}_2$—), 2.25-2.38 (144H, m, —C$\underline{H}_2$C(O)—, (4m)-C$\underline{H}_2$—), 3.97-4.11 (256H, m, —C(O)OC$\underline{H}_2$CH$_3$), 4.15-4.34 (136H, m, Ar—O—C$\underline{H}_2$—, (2,2',2",2'")-C$\underline{H}$(NH)—), 6.82-7.09 (4H, broad, Ar), 7.71-8.23 (128H, broad, Ar, —N$\underline{H}$—), 8.72-8.94 (8H, m, broad, Pyr).

P-Glu$^4$.

11 (0.4 g, 0.02 mmol) was dissolved in THF (100 ml), NaOH (1.0 g, 25.6 mmol) and water (0.5 ml) were added to the solution, and the mixture was allowed to react overnight under stirring at r. t. The precipitate formed was collected by centrifugation, dissolved in aq. NaOH (0.1M, 20 ml) and stirred for additional 6 h at r. t. The following work up and purification followed that for C1-Glu$^3$, C1-Glu$^4$ and C2-Glu$^4$. The title dendrimer (sodium salt) was isolated as a green solid. Yield: 0.305 g, 90%.

Synthesis of UCNP-Dendrimers

In a typical procedure for modification of UCNP's with organic ligands (9), a solution of UCNP's (~20 mg/ml) pre-treated with NOBF$_4$ in DMF was added to a stirred aqueous solution of a dendrimer (or PAA) (~60 mg/ml), so that the total ratio (by mass) of UCNP/organic ligand was ~1:2. The mixture was stirred overnight at r. t., then centrifuged at 10,000 g for 1-3 h. To remove the excess of the ligand and traces of DMF, the obtained precipitate was re-dissolved (or re-dispersed) in distilled water and precipitated again by centrifugation. This procedure was repeated 3 times.

1H and 13C NMR spectra were recorded on a Bruker DPX-400 spectrometer operating at 400.1 or 100.6 MHz, respectively. Mass spectra were recorded on a MALDI-TOF Bruker Daltonics Microflex LRF instrument, using α-cyano-4-hydroxycinnamic acid (CCA) as a matrix in positive-ion mode. Optical spectra were recorded on a Perkin-Elmer Lambda 35 UV-Vis spectrometer. Steadystate luminescence measurements were performed on FS920 spectrofluorometer (Edinburgh Instruments), equipped with an R2658P photomultiplier (PMT) (Hamamatsu). Quartz fluorometric cells (1-cm path length; Starna) were used in optical experiments. DLS measurements were carried out on a Zetasizer NanoS instrument (Malvern). TEM images were acquired on a JEM-1400 microscope (Jeol) using a 120-kV accelerating voltage.

Calculations

To evaluate the geometries of the dendrimer cores, calculations were performed using the DFT method, as implemented in Gaussian 03 (Rev. D.01, Intel EM64T/AMD, Gaussian, Inc). (10) The structures of cores C1' (C1 without aminobutyrate extension arms), meso-tetra-3,5-dimethoxyphenylporphyrin (P') (a prototype of porphyrin P), and C2 were optimized using B3LYP/6-31G(d) model chemistry, beginning with AM1-optimized structures. A structure of core C1', in which the peripheral aryl rings are fixed at 90° with respect to the central benzene ring, was also computed using the same model chemistry. Frequency calculations were ran on the equilibrium structures to confirm the stationary points.

To facilitate comparison between equilibrium and non-equilibrium (90°) structures of C1' pure electronic energies were used. These were found to be:

$$C1'(\text{equilibrium})-E=-2969.67360279 \text{ Ha}$$

$$C1'(90°)-E=-2969.66534351 \text{ Ha}$$

Simulations involving dendritic macromolecules were performed using AMBER force field as implemented in HyperChem 7.0 (HyperCube Inc.). Water was modeled as a distance-dependent dielectric continuum (scale factor 4). Molecular dynamics simulations were ran typically at 1000° C., a conformation was selected and the energy was minimized 8-10 conformations were sampled for each scenario. The surface was modeled as a single-sheet LiF. Simulations at this level of course cannot reproduce the actual surface effects (e.g. surface long-range potential was not explicitly taken into account), but rather serve as an illustration of the geometrical considerations underpinning our design. Nevertheless, even at this level it is apparent that there are significant differences between the conformations that the molecules studied can adopt near surfaces.

Molecular cross-sections of the dendrimers were calculated by taking several measurements across their molecular skeletons, averaging them and finding the areas of the corresponding circles.

The fluorescence quantumyields of P-Glu$^4$ and UCNP/P-Glu$^4$ were measured against fluorescence of Rhodamine 6G in EtOH (Φfl=0.94) (53). Scattering spectra of UCNPs modified with dendritic ligands and PAA were obtained by synchronously scanning excitation and emission monochromators of the fluorometer while recording the corrected emission signal. For steady-state measurements of UCNP emission via upconversion, a compact CW laser diode (max=980 nm) was placed inside the fluorometer and used as an excitation source. The beam of the diode was directed at the optical cell at the right angle relative to the detector. A short-pass filter (900-nm cutoff; Asahi Spectra) was inserted into the emission path. Emission spectra were corrected by response curve of the PMT. For power-dependence measurements, the incident power on the sample was varied by using neutral density filters and measured by an optical power meter (Coherent). The beam was not focused in the power-dependence measurements.

Time-resolved measurements of emission via upconversion were performed using a setup for cellular two-photon phosphorescence lifetime microscopy. In vivo imaging was performed in epi-fluorescence mode using a system based on a commercial twophoton microscope (Ultima; Prairie Technologies). The excitation was provided by a Ti:sapphire oscillator (100-fs pulsewidth; 80-MHz repetition rate; Mai-Tai HP; Spectra Physics). Beamfocusing and collection of emissionwere accomplished by a water-immersion lens (20×; NA 0.95; XLUMPLFI; Olympus). Three-dimensional median filter and histogram equalization were used for image processing.

For vascular imaging, C57BL mice (male; 25-30 g; 10-12 wk old) were anesthetized by isoflurane (1-2% in a mixture of O2 and N2O) under constant temperature (37° C.). A cranial window was made in the parietal bone, the dura was removed, and the window was sealed with a 150-μm-thick microscope coverslip. During imaging, blood pressure and blood gases were monitored via the catheter inserted into the femoral artery, which also served for administration of probes. All experimental procedures were approved by the Massachusetts General Hospital Subcommittee on Research Animal Care.

Elemental Analysis

The elemental analysis (C, H, N) by combustion was performed in the Micro-Analysis Inc. laboratory (Delaware, USA). UCNP-dendrimers and UCNP-PAA were obtained by reacting UCNP's with aqueous solutions of the organic ligands. The dendrimers were purified by dialysis and assumed to be retained in solutions as sodium salts, i.e. all m carboxylate groups in the dendrimer are complexed with $Na^+$, i.e. $CO_2Na$. All samples were extensively dried in vacuum prior to the analysis.

TABLE 1

Results of elemental analysis.

| Sample | % C | % H | % N |
|---|---|---|---|
| C2-Glu[4] | 35.24 | 4.54 | 7.65 |
| C1-Glu[4] | 38.00 | 4.74 | 8.30 |
| UCNP/C2-Glu[4] | 4.66 | 0.64 | 0.74 |
| UCNP/C1-Glu[4] | 6.04 | 0.76 | 1.04 |
| UCNP/PAA | 4.04 | 0.44 | 0.00 |

Estimation of number of organic ligands (dendrimers and PAA) adhered to UCNP surface Abbreviations:
 m—mass of the ligand as a sodium salt.
 Δm—mass of $Na^+$ ions in the sodium salt.
 M—mass of UCNP.
 k—number of ligand molecules per UCNP.

(The nanoparticle mass (M) was calculated assuming ideal spherical geometry, r=10 nm radius. The density was calculated for undoped $Na_{1.5}Y_{1.5}F_6$ hexagonal bipyramidal crystals: a=5.973, c=3.529 Å. (11) M=281.83 g/mol; ρ=4.5 g/cm$^3$. The mass of a single UCNP was found to be $18.84 \times 10^{-18}$ g. The surface area of the sphere is 1256 nm$^2$.)

Using these abbreviations, the mass of UCNP modified with k organic ligands is: k×(m−Δm)+M.

Here for simplicity it was assumed that upon interaction with the surface, all $Na^+$ ions are replaced by the ligand-UCNP contacts. The error introduced by this assumption is rather small, since the fractional mass of $Na^+$ ions (kΔm) in the overall modified UCNP is not large (e.g. <2% error for UCNP/C1-Glu[4], even assuming all of its sodium atoms are retained).

Thus, the fractional mass of organic material in modified UCNP is expressed as:

$$f_{org} = k \times (m - \Delta m) / [k \times (m - \Delta m) + M] \quad (1)$$

The following calculations are concerned specifically with UCNP/C1-Glu[4] and UCNP/C2-Glu[4].

C1-Glu[4] sodium salt: $C_{678}H_{790}N_{128}O_{384}Na_{128}$, MW 19806

C2-Glu[4] sodium salt: $C_{246}H_{294}N_{48}O_{144}Na_{48}$, MW 7326

% Na (fractional mass) of Na atoms in these dendrimers (as sodium salts) can be expressed as: % Na=(23/14)×% N (the numbers of Na and N atoms are equal). Thus:

$$(m - \Delta m) = m \times (1 - (23/14) \times \%N) \quad (2)$$

Assuming the number of C atoms in the dendrimer is x, % C in the dendrimer is found as:

$$\%C = 12x/m, \text{ or } 12x = \%Cm. \quad (3)$$

In UCNP/dendrimers fraction mass of C atoms is found as:

$$\%C' = k \times 12x / (k \times (m - \Delta m) + M), \text{ or}$$

$$\%C' = k \times \%Cm / [k \times (m - \Delta m) + M], \text{ and}$$

$$[k \times (m - \Delta m) + M] = (km\%C) / \%C'. \quad (4)$$

Substituting (2) and (4) into (1) we find that:

$$f_{org} = (1 - (23/14) \times \%N) \times \%C' / \%C \quad (5)$$

UCNP/C2-Glu[4]: $f_{org} = 11.6$

UCNP/C1-Glu[4]: $f_{org} = 13.7$

Similar calculations give:

UCNP/PAA: $f_{org} = 8.1$

Based on the above results molecules adhere UCNP surfaces with the following surface densities:

1) PAA—~550 molecules per nanoparticle (1 molecule per ~2.3 nm$^2$);

2) UCNP/C1-Glu[4]-106 molecules/particle (1 molecule per 11.8 nm$^2$);

3) UCNP/C2-Glu[4]-237 molecules/particle (1 molecule per 5.3 nm$^2$).

Figure 7:
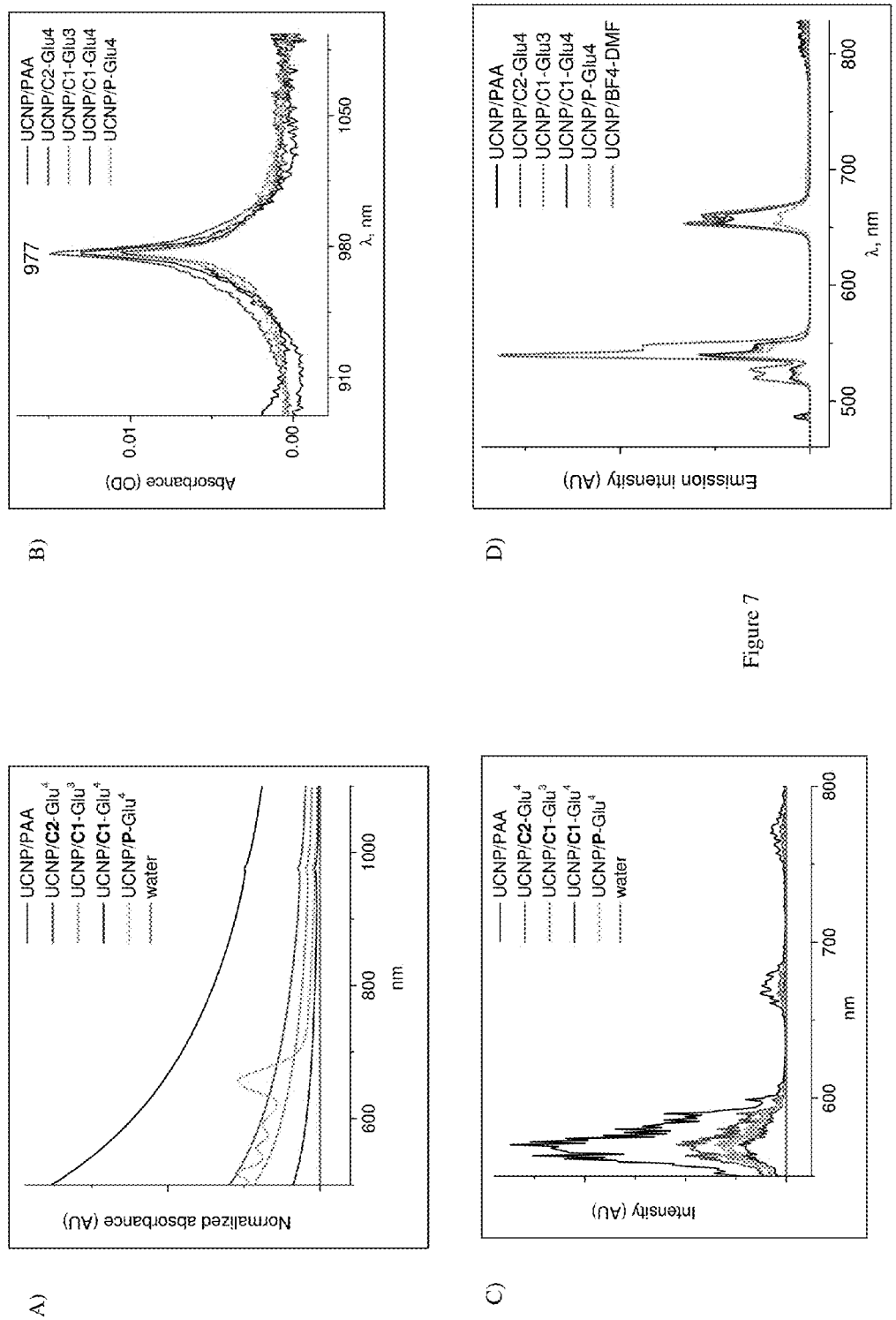
FIG. 7 shows (A) absorption spectra of UCNPs modified with dendritic ligands and PAA, normalized by the integrated intensity of the $Yb^{3+}$ absorption band ($\lambda_{max}$=977 nm). (B) absorption spectra of UCNPs modified with dendritic ligands and PAA near 980 nm. The scattering baseline was subtracted. (C) scattering spectra of UCNPs and dendritic ligands, normalized by the integrated intensity of the $Yb^{3+}$ absorption band ($\lambda_{max}$=977 nm). (D) emission spectra of UCNPs and dendritic ligands ($\lambda_{ex}$=980 nm), normalized by the integrated intensity of the $Yb^{3+}$ absorption band ($\lambda_{max}$=977 nm).

From calculations, average cross-sections of C1-Glu[4] and C2-Glu[4] were found to be ~11 nm$^2$ and 4.7 nm$^2$, respectively (see Optical Properties, FIG. 7).

pH Titrations of UCNP/P-Glu[4]

pH titrations were performed at 22° C. using solutions of P-Glu[4] or UCNP/P-Glu[4] HEPES buffer (15 mM) or in distilled water. pH was adjusted by addition of HCl or KOH. For measurements by absorption, absorbances of solutions at Soret peak maxima were kept below 1.0 OD. For measurements by emission and two-photon excitation, solutions containing ~10 mg/ml of UCNPs were used.

The titration curves were constructed by plotting absorbances at selected wavelengths, or, in the case of fluorescence, integrated emission bands vs pH. In ratiometric titrations, ratios of the integrated emission bands upon excitation at 980 nm were plotted vs pH. The titration data were fitted to standard sigmoidal curve with an extra parameter n to account for heterogeneity of the sample and multiple interfering protonation reactions of porphyrin-dendrimers on the nanoparticle surface:

$$S_{\lambda 1}(pH) = P_1 \frac{10^{n(pH-pK)}}{1 + 10^{n(pH-pK)}} + P_2$$

Fitting was performed using Microcal Origin software (Origin 7.0).

Results

Example 1

Producing Water-Soluble Upconverting Nanoparticles (UCNPs)

Researches have recently developed a facile synthetic method for accessing highly monodisperse β-NaYF4-based UCNPs with distinct sizes/morphologies and bright luminescence, tunable by addition of different lanthanide dopants. UCNPs are synthesized through thermal decomposition of commercially available sodium and lanthanide trifluoroacetates, which are heated in a mixture of oleic acid and 1-octadecene, while a molten salt bath is used as a heat reservoir. This methodology and the subsequent primary surface functionalization using nitrosonium borate (NOBF4), also developed recently, render UCNPs suitable for surface modifications via anion exchange approach.

Conventional polymeric ligands, e.g. polyacrylic acid (PAA) or polyetyleneamine (PEA), have been used to displace $BF_4^-$ ions and to surface-coat UCNPs. Such particles show somewhat improved hydrophilicity, but still do not form true aqueous solutions. Even after modification of free carboxylic groups on the primary ligands (e.g. PAA) with polyethyleneglycols (PEG) fragments, the resulting particles do not gain significantly in water solubility. We believe that at least one reason for that is the fact that the majority of carboxylic groups on e.g. PAA become engaged in interactions with surface groups on the nanoparticles, while only a few of the remaining caboxylates remain available for interactions with the solvent (water) or for surface reactions (e.g. with PEG-amines).

Dendrimers are branched macromolecules that exhibit well-defined structures and high degree of topological order. From the structural point of view, dendrimers contain three distinct regions: core, branches and surfaces. Chemically, dendrimer surfaces comprise many identical functional groups, which can be chosen to be ionic, neutral hydrophilic, hydrophobic or have a particular chemical reactivity. Our approach is as follows. Assuming for simplicity that a dendrimer has spherical shape and its surface groups are anionic (e.g. carboxylates), a "patch" of the dendrimer surface can become engaged in electrostatic interactions with UCNP surface by way of displacing weakly bound $BF_4^-$ ions. As a result, the dendrimer will adhere to the UCNP surface just like a tennis ball would stick to a Velcro-coated wall. Binding of dendrimers will be cooperatively enhanced because multiple groups in the patch interacting with the UCNP. Not a single, but many dendrimers will bind to a UCNP because the size (diameter) of even a small UCNP (20-30 nm) is typically ca 10 times larger than the size of even a large dendrimer (2-3 nm). Because dendrimers are pseudo-spherical in shape, only some of their surface groups will interact with the surface of the UCNPs. The remaining groups will remain in contact with the solvent, thus enhancing the solubility of UCNP in aqueous environments. Alternatively, these groups will be suitable for chemical modifications in order to tailor the UCNP properties.

One important advantage of the solubilizaton scheme is that dendrimers can be chosen to bear functional motifs at their cores, e.g. optically-active or electro-active units, such as organic dyes, metalloporphyrins or other motifs. Thus, in addition to solubilizing and enabling functionalization, the proposed method will enable preparation of UCNPs with secondary functionalities.

One important addition to make here is that in principle not only dendrimers but any hyperbranched polymers containing multiple hydrophilic ionic groups should be suitable for similar surface modification of UCNPs.

The preparation of soluble UCNPs is accomplished in three steps as described below. The first two steps are needed for preparation of precursor UCNPs, suitable for modification with dendritic ligands. The methodology used in these steps was described and published earlier by other researchers. See e.g., Ye et al., 2010, PNAS, vol. 107, pages 22430-22435. It is important to realize that although these methods are extremely useful, they are not the only ones that can be used for our purpose. There is a number of alternative methods described in the literature (for review see, for example, ref. [3]1) that allow synthesis of UCNPs with high monodispersity and bright luminescence, and some of them can also be used in our scheme as well. See e.g., Mader et al., 2010, Current Opinion in Chemical Biology, vol. 14, pages 582-596. The improved technology disclosed herein is concerned specifically with surface modification of UCNPs using dendrimers (Step 3 below). The overall proposed scheme is illustrated in Scheme 1.

Steps Involved in Preparation of Soluble UCNPs:

In Step 1 UCNPs supported by capping ligands (such as PEA or PAA) are synthesized by the thermal decomposition method, hydrothermal method or any other suitable method. The thermal decomposition method, developed recently by Ye et al is superior in that it allows preparation of highly monodisperse UCNPs with tunable emission and high up-conversion efficiency.

In Step 2, ligand exchange strategy is used to replace original hydrophobic capping ligands with ligands possessing functional groups suitable for further modification. A convenient strategy has recently been developed by other researchers, which includes modification of UCNP surfaces by way of treating them with $NOBF_4$. The replacement of the original organic ligands (i.e. oleic acid) by $BF_4^-$ ions renders UCNPs with remarkable solubility in polar solvents, such as dimethylformamide (DMF), dimethylacetimaide (DMA), dimethylsulfoxide (DMSO) etc., without affecting the UCNP size distributuion, shape and optical properties. Due to the relatively low binding affinity of $BF_4^-$ ions to UCNP surfaces, $BF_4^-$ modified UCNPs readily undergo secondary surface modification. For example, $BF_4^-$ modified UCNPs can be modified by such polymeric ligands as PAA or PEA, taking advantge of the cooperative binding of these ligands to UCNP surfaces due to their poly dentate nature. In one variant of the disclosed approach (see Scheme 1, Route 2), such UCNPs, pre-modfied with PAA, PEA or other similar ligands, serve as intermediates for construction of UCNP-dendrimer particles.

Step 3 is the key step in the described approach, and it is depicted in Scheme 1. As an example, we chose polyglutamic dendrimers containing porphyrin or metalloporphyrin cores. Such dendrimers are routinely prepared in our laboratory, and therefore it was convenient to use them in our proof-of-the-principle experiments.

The scheme depicts two modification methods, which result in functionally identical, but structurally slightly different dendritic UCNPs. Both methods (Routes) are disclosed in this application. In a more straightforward route (Route 1), $BF_4^-$ ions are displaced directly by polyanionic dendrimers, such as polycarboxylic porphyrin-dendrimers (shown in the middle). Our preliminary experiments confirm that this direct route is feasible and leads to UCNPs possessing good aqueous solubility in the physiologial pH range. We attribute such high aqueous solubility to a large number of free carboxylate groups, only a part of which is involved in the binding to the UCNP surfaces.

The overall process involves: a) hydrothermal synthesis of UCNPs with capping oleic acid ligands; b) ligand exchange of the capping ligand(s) onto $BF_4^-$ anions; and c) simple mixing of solutions of UCNPs in DMF or similar solvents with aqueous solutions of dendrimers.

The dendritically modified UCNPs can be isolated upon acidification of the resulting solutions, followed by collection of the modified nanoparticles by simple centrifugation. Polyglutamic porphyrin-dendrimers of different generations were tested in this scheme (vide infra); and dendrimers of higher generations gave UCNPs with higher aqueous solubility. For example, UCNPs with the diameter of ca 20 nm could be completely solubilized in water using generation 4 (Gen 4) polyglutamic dendrimer, having tetracarboxyphenylporphyrin as a core.

In Route 2, UCNPs were modified with dendritic fragments (either dendrimers or dendrons) in covalent fashion, starting from UCNPs pre-modified with polyacrylic acid (PAA). The latter were obtained from UCNPs with surface $BF_4^-$ ions by the same ligand-exchange strategy but using aqueous solution of PAA. Functional groups ($NH_2$ or $CO_2H$) of the primary polymeric ligands (e.g. PAA or PEA) not engaged in interactions with UCNPs, are modified covalently with orthogonally functionalized dendrimers. For example, PEA-coated UCNPs are modified with polycarboxylate dendrimers.

Depending on the intended use, the peripheral groups (e.g. carboxyls) on the dendrimers are PEGylated by e.g methoxypolyethyleneglycolamine (PEG-$NH_2$), rendering neutral hydrophilic UCNPs. These PEGylated nanoparticles could be purified and isolated by size-exclusion chromatography (SEC). The presence of the colored porphyrin core simplified detection of the bands during the SEC separation and thus assisted the purification process. The resulting UCNPs exhibit high aqueous solubility and retain excellent up-conversion efficiency.

Pegylation step might be useful for preventing interactions of UCNPs with biological macromolecules if, for example, non-specific blood-pool contrast enhancing UNPS are required. Alternatively, peripheral groups on the dendrimers, not engaged in bonding with UCNP surfaces can be used for linking UCNPs to various targeting moieties, such as antibodies or cell-targetic peptides. Linking can be achieved using conventional peptide chemistries or other standard methods.

We performed initial measurements of photophysical properties of UCNPs. Both rise and decay time constants of the UCNP emission upon multiphoton excitation ($\lambda_{max}$=980 nm) were measured, using a special multiphoton phosphorescence lifetime microscopy setup. It should be mentioned that the nanoparticles are several times smaller than the size of the diffraction-limited excitation volume (considering optical wavelengths), so UCNPs could not be observed as individual species. However, their photophysical parameters could be measured with high accuracy, confirming that these materials are suitable for multiphoton microscopy applications.

In summary, we have demonstrated that UCNPs of different sizes, ranging from ca 20 to ca 100 run in diameter, can be modified with polyglutamic dendrimers bearing carboxylic groups at the periphery. The described above steps provide a simple and straightforward approach to soluble nanoparticles, e.g. UCNPs, for biological applications. The approach is enabled by unique structural features of dendrimers, i.e. multiple peripheral functional groups and pseudo-spherical shape.

Example 2

Polyglutamic Dendrimers

To functionalize UCNPs, polyglutamic dendrimers were chosen because of their very high aqueous solubility throughout physiological pH range, their excellent biocompatibility, and their lack of toxicity, as evidenced by numerous studies using them as in vivo oxygen probes. In contrast, popular commercial amino-terminated dendrimers are less hydrophilic and may induce toxicity. To facilitate formation of globular structures, tetrameso-3,5-dialkoxyarylporphyrin (P) was selected as the initial core fragment (FIG. 8A). Meso-aryl substituents in P are rotated ~73° relative to the tetrapyrrolic macrocycle, directing eight anchor groups above and below its plane.

Figure 9:
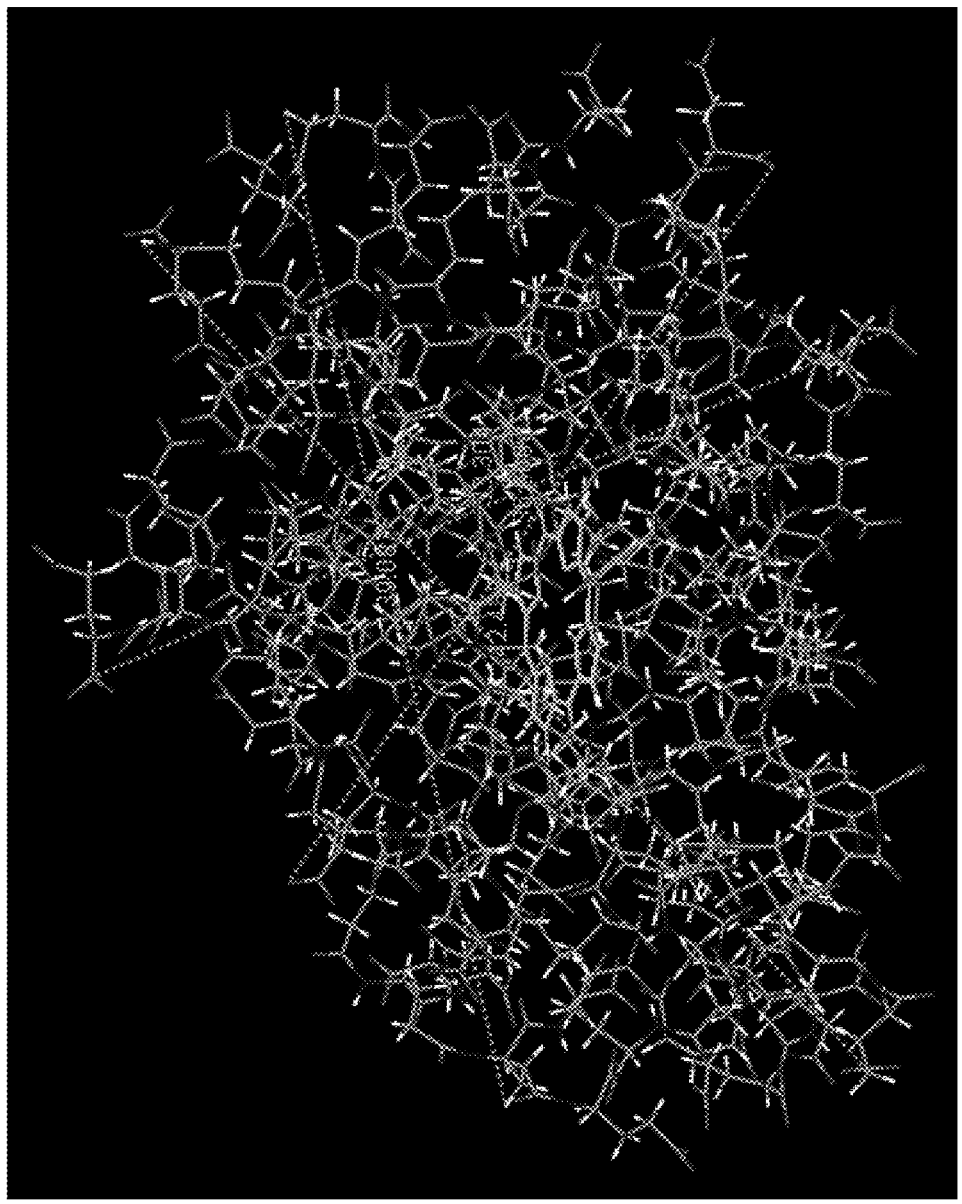
FIG. 9 shows a structure of P-Glu$^4$. The average molecular diameter, determined by taking several measurements across the molecular skeleton, is 3.9 nm.

Generation (Gen) 4 polyglutamic dendrons (FIG. 8G) are capable of complete encapsulation of the core porphyrin, giving pseudoglobular dendrimers ~3.9 nm in diameter (FIG. 9). Conversely, conformations in which all peripheral carboxylates point to the same direction, capable of binding to a surface, are energetically unfavorable.

Figure 10:
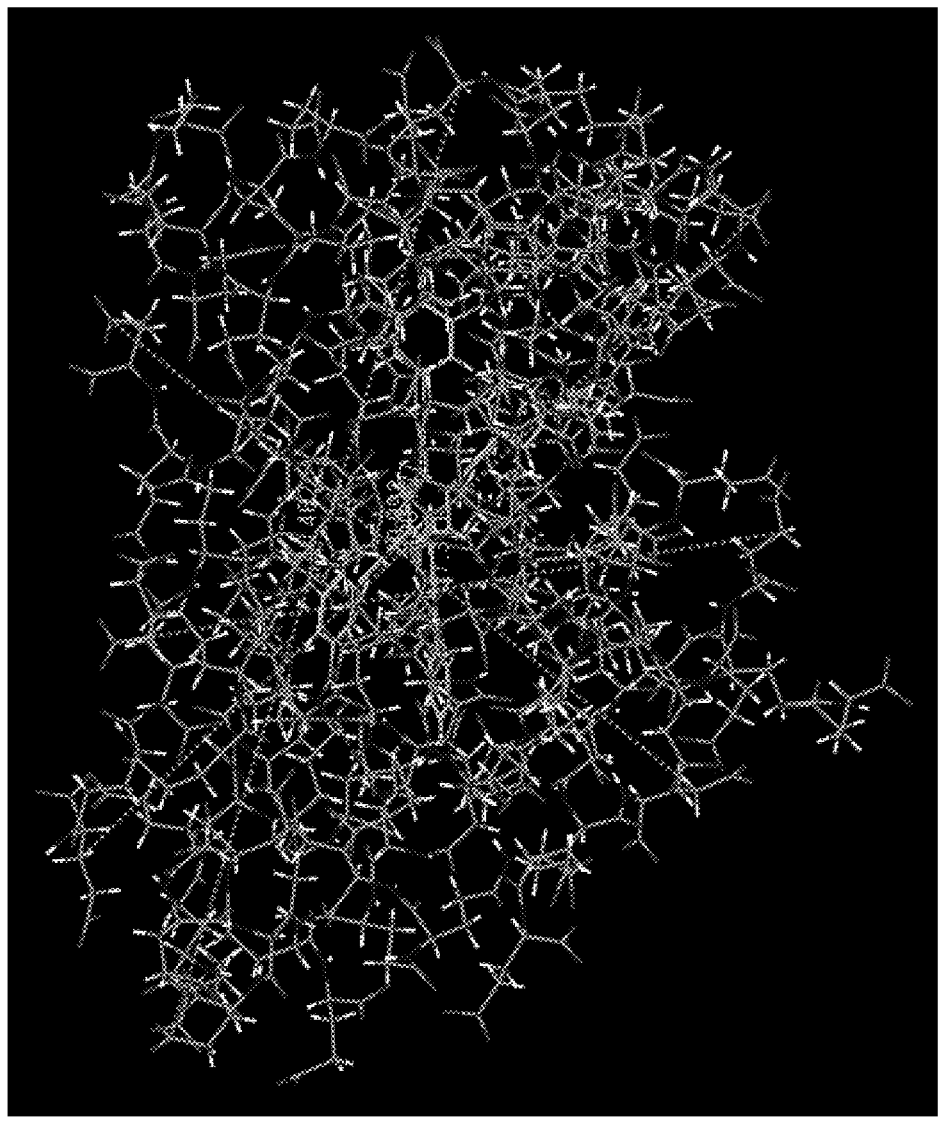
FIG. 10 shows a structure of C1-Glu$^4$. The average molecular diameter, determined by taking several measurements across the molecular skeleton, is 3.8 nm.
Figure 11:
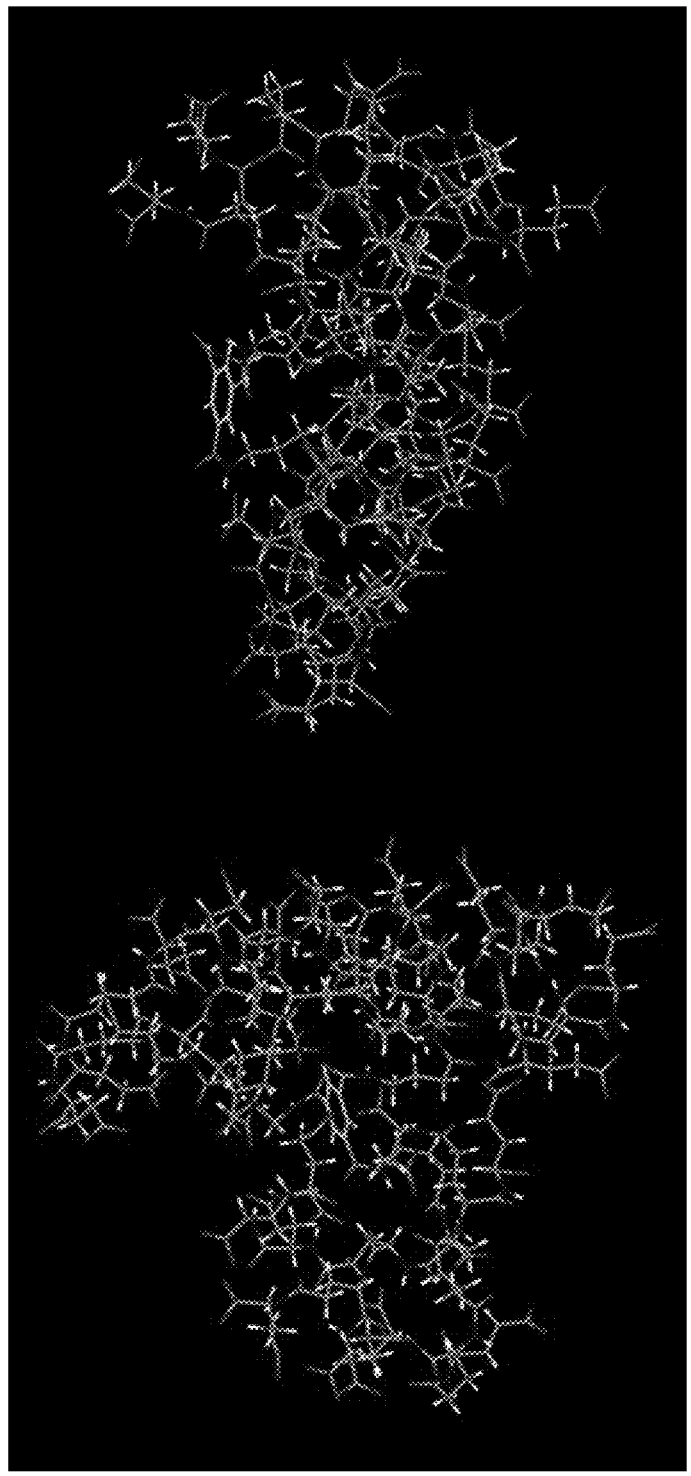
FIG. 11 shows two conformations of C2-Glu$^4$. The three flexible dendritic arms can easily adopt a conformation (right) where many of their termini occur "on the same side" of the molecule.

Porphyrins possess strong visible absorption bands, which overlap with emission of $Er^{3+}$- doped UCNPs. This property turned out to be extremely useful in designing upconverting pH nanosensors (vide infra). However, to construct imaging probes, we chose dendrimers with equally rigid but noncolored core C1 (FIG. 8B), dimension-wise resembling tetraarylporphyrins. In relaxed C1, peripheral aryls are tilted ~25° relative to the central benzene ring; however, the conformation in which all four aryls are orthogonal to the central ring is only 5.2 kcal/mol higher in energy. Upon decoration with bulky dendrons, these aryls are expected to rotate, facilitating formation of pseudoglobular structures (FIG. 10). Use of the γ-aminobutyrate extension arms in C1 (FIG. 8B) was essential for increasing the core solubility, as well as improving the yield of coupling reactions. In addition to P and C1, 1,3,5-benzenetricarboxylic acid (C2) (FIG. 8C) was used in this study for comparison. C2 has only three anchor groups, and, in Gen 4 C2-dendrimers, peripheral crowding should be much less pronounced. Therefore, C2-dendrimers may be expected to bind to UCNPs by engaging most of their carboxylates into surface interactions (FIG. 11). Gen 3 and 4 polyglutamic dendrons (Glu3 and Glu4) (FIG. 8G) were synthesized by the convergent method from N-tert-butoxycarbonyl protected L-glutamic acid and diethyl L-glutamate, using standard peptide coupling/deprotection chemistry (see Materials and methods: Synthesis). Decoration of P, C1, and C2 with the Glu dendrons after hydrolysis (which may have led to partial racemization) gave highly monodisperse water-soluble dendrimers PGlu$^4$, C1-Glu3, C1-Glu$^4$, and C2-Glu$^4$ with 128, 64, 128, and 48 peripheral carboxylates, respectively. Purity of the compounds was confirmed by MALDI-TOF and NMR analysis.

Example 3

UCNP Synthesis and Surface Modification

Synthesis of core nanoparticles and efficient procedure for removal of the primary hydrophobic capping layer is a prerequisite for obtaining hydrophilic UCNPs. We used hexagonal phase β-NaYF4-based nanocrystals, doped with Yb$^{3+}$ (20%) and Er3$^+$ (2%), which comprise one of the brightest known upconverting materials. Highly monodisperse spherical nanoparticles, 23±1 nm in diameter, were prepared by thermal decomposition of trifluoroacetate salts in the presence of oleic acid. The oleate capping ligands were removed via the treatment with NOBF4, rendering UCNPs coordinated by BF4– ions. The latter can readily undergo exchange reactions with a variety of ligands (e.g., PAA). Importantly, no heating is required for completion of these steps, thus permitting use of even labile organic molecules for UCNP modification.

The nanoparticles were dendrimerized by simple mixing of dimethylformamide (DMF) solutions of UCNP-BF4– with aqueous solutions of dendrimers at room temperature. For comparison, UCNPs were also modified with PAA (average molecular mass, 1,800 Da), a common ligand for nanoparticle solubilization. Right after mixing, all solutions appeared optically clear, but upon centrifugation, which was necessary to remove DMF and unreacted ligands, UCNP/C1-Glu3 and UCNP/C1-Glu$^4$ produced pale yellow soluble gels, whereas UCNP/PAA and UCNP/G2-Glu$^4$ precipitated as dense residues. Attempts to redissolve these precipitates (FIG. 8I) gave milky suspensions. UCNP/P-Glu$^4$ also gave a soluble gel, albeit dark green in color (FIG. 8J).

Aqueous solutions of UCNP adducts with C1-Glu3, C1-Glu$^4$, and P-Glu$^4$ were found to be stable at pH 5-12 at 22° C. and could be stored for months at high concentrations (~200 mg/ml) or directly as gels without noticeable degradation. Remarkably, UCNP/P-Glu$^4$ was stored for over 1 y in solution (20 mg/ml), with no detectable loss of transparency. Acidification of UCNP/dendrimer solutions to pH3-4 led to a slurry-like appearance but could be reversed back to transparency upon increase in pH. Drying of all of the above materials led to irreversible loss of solubility.

Example 4

Properties of UCNP/Dendrimers

Differences between UCNPs modified by different ligands are immediately apparent in their scattering spectra (FIGS. 7A and 7C) and can be detected easily by the naked eye (FIGS. 8 I, K, and L), for example, by looking at luminescent traces produced by excitation with a handheld laser. A beam passing through a solution of UCNP/C1-Glu$^4$ (FIG. 8K) was scattered only weakly and retained enough power to excite UCNP/C2-Glu$^4$ in a cuvette placed behind. However, when the order of the samples was switched, no luminescence of UCNP/C1-Glu4 was detectable because of the strong scattering by UCNP/C2-Glu$^4$.

Dynamic light scattering (DLS) (FIG. 8H) provided insight into the solution properties of the UCNP/dendrimers. Consistent with the presence of individual non-aggregated nanoparticles, UCNP/C1-Glu3 and UCNP/C1-Glu$^4$ (20 mg/mL) exhibit narrow size distributions, centered near 35-40 nm. These species are larger than original UCNPs (~23 nm in DMF), presumably because of hydrated dendritic coats, but smaller than interparticle aggregates, which would be expected to show sizes at least twice the diameter of individual nanoparticles. In contrast, UCNP/C2-Glu$^4$ and UCNP/PAA reveal broad size distributions with maxima near 120 and 100 nm, respectively.

Figure 12:
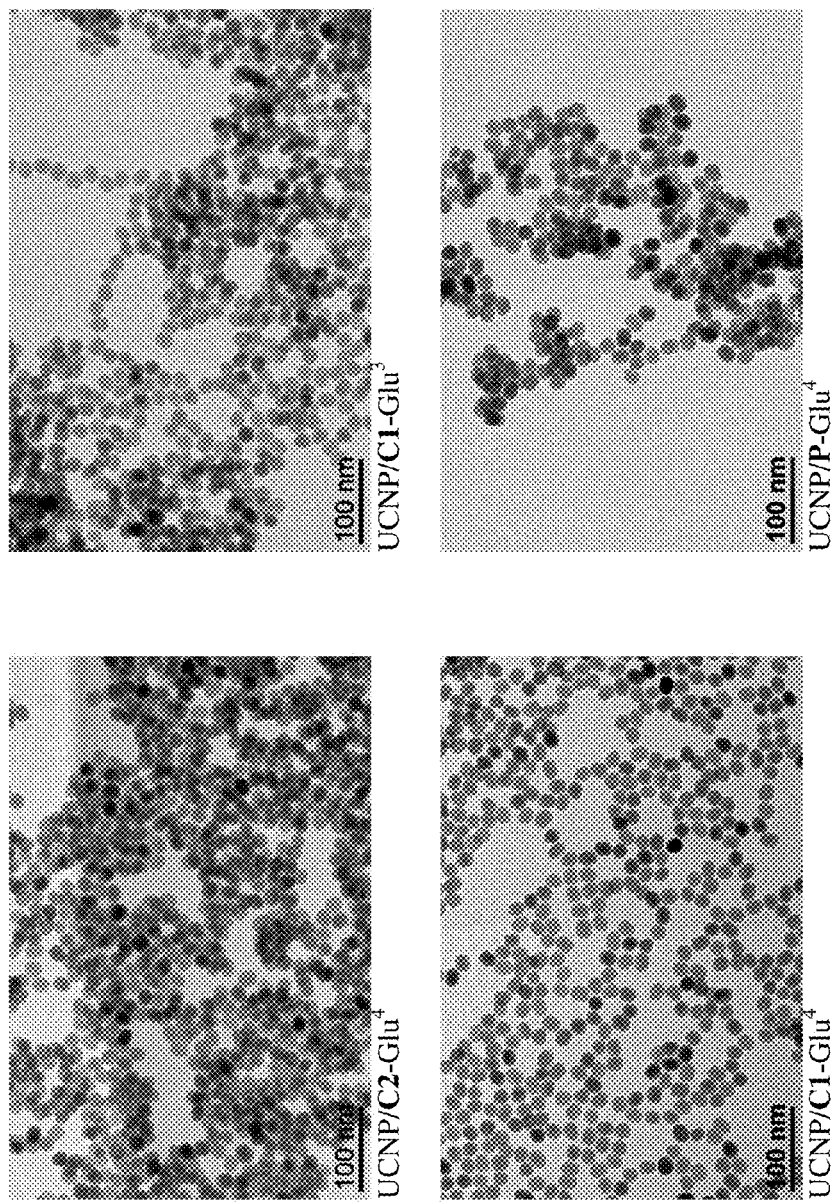
FIG. 12 shows transmission electron microscopy (TEM) imaging of aggregation trends in the solid state.

Transmission electron microscopy (TEM) (FIGS. 8 M and N, and FIG. 12) shows the same aggregation trends in the solid state as seen in solutions. For example, UCNP/C1-Glu$^4$ (FIG. 8N) emerges in TEM images as individual nanoparticles, whereas images of UCNP/PAA (FIG. 8M) show chunks of aggregated material.

The number density of ligand molecules per UCNP was calculated based on the elemental analysis (See material and methods: Elemental analysis). In all cases, surfaces of UCNPs appear to be densely covered by the ligands; and the total number of carboxylate groups per nanoparticle is nearly the same for all ligand types (~12,000). At the same time, experiments (above) clearly show that UCNPs modified with C1-Glu3, C1-Glu$^4$, and P-Glu$^4$ exhibit much better solubility than those covered with C2-Glu$^4$ and PAA. This result suggests that it is not the total number of carboxylates but rather the ratio between bound and unbound carboxylate groups that governs the solubility. It follows that the fraction of the surface bound carboxylates must be different between different ligand molecules. We hypothesize that this fraction depends on the shape that a molecule adopts upon binding to the surface.

Figure 13:
FIG. 13 shows simulations of surface bound PAA and polyglutamic dendrimers. Fully ionized molecules of PAA (25 carboxylates), C2-Glu$^4$ and C1-Glu$^3$ were placed near a model surface (LiF, single sheet) and subjected to molecular dynamics simulations, followed by energy minimization (see S15 for details). Out of 25, 15 carboxylates (~60%) in PAA became engaged with the surface. (Bound carboxylates are shown in green). In the case of C2-Glu$^4$, 30 out of 48 carboxylates (~62%) turned to the surface; while only 18 out of 64 carboxylates (28%) of C1-Glu$^3$ adhered to the surface, leaving 46 carboxylates (72%) free in contact with solution.

To examine this hypothesis, we performed molecular simulations (FIG. 13), which revealed that a linear molecule (PAA) can indeed easily adopt conformations in which over 60% of carboxylates become surface-bound. Likewise, dendrimer C2-Glu$^4$, possessing small trifunctional core, can flatten on the surface and donate 60-65% of its termini to the surface interactions. However, C1-Glu$^3$, having almost the same number of carboxylates as C2-Glu$^4$ but a rigid octa-functionalized core, is able to engage only ~18% of its carboxylates with the surface, while retaining ~72% interacting with solvent.

Combining these results with estimated surface coverage (from the elemental analysis), we can deduce that the larger solubilizing capacity of, for example, C1-Glu$^4$ comes from as many as ~10,200 free carboxylates per nanoparticle, making up the interface with the solvent, whereas in the case of UCNP/C2-Glu$^4$, this number is significantly less (ca. 4,300). Thus, the dendrimer core appears to play an important role in defining the solubilizing capacity.

Figure 14:
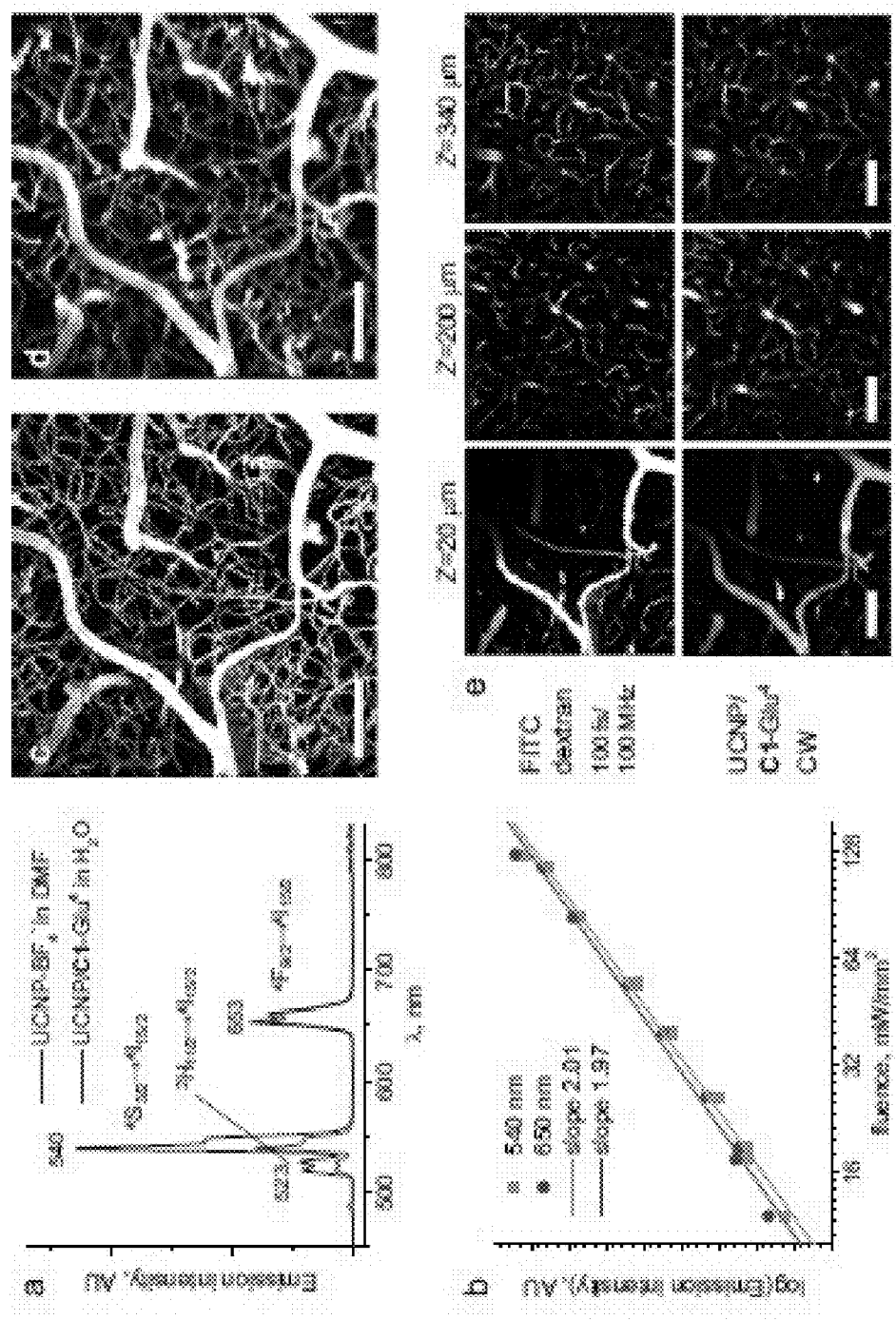
FIG. 14 shows (A) emission of UCNP-BF$_4$—in DMF and UCNP/C1-Glu4 (in H$_2$O) induced by CW excitation at 980 nm. The samples contain equal amounts (by weight) of inorganic UCNPs. (B) Dependence of emission intensity at 540 and 650 nm for UCNP/C1-Glu4 on the incident power (log-log plot). A nonfocused beam (1.5 mm in diameter) was used in this experiment (see materials and methods). (C-E) Mouse brain imaging. (C) Maximal intensity projection (MIP) image of a 200-nm-thick image stack, from the surface down, acquired using FITC-dextran and a mode-locked Ti:sapphire laser (100 fs; 80-MHz repetition rate; 800-nm excitation wavelength). (D) MIP image of the same stack obtained with UCNP/C1-Glu$^4$ and the same laser operating in CW mode at 980 nm. (E) MIP images acquired at different depth. Stacks extend 20 nm down from the level marked above. (Scale bars: 100 nm.)

Except for UCNP/P-Glu$^4$, the absorption spectra of UCNP/dendrimers in the visible region are dominated by scattering, but in addition, they show a characteristic Yb$^{3+}$ band (λmax=977 nm). Excitation into this band induces upconverted emission, which resembles that of nondendrimerized UCNPs (FIG. 14A). The three main visible bands (max=527 nm, λmax=539 nm, and λmax=653 nm) correspond to the radiative transitions of Er$^{3+}$ ion ($^2H_{11/2} \rightarrow ^4I_{15/2}$, $^4S_{3/2} \rightarrow ^4I_{15/2}$, and $^4F_{9/2} \rightarrow ^4I_{15/2}$). The second order of excitation was confirmed by recording power dependencies of emission intensities (FIG. 14B). Compared with the UCNP- BF4 in DMF, the green-to-red emission ratio in UCNP/dendrimers appears to be attenuated (FIG. 14A), suggesting stronger quenching of the $^2H_{11/2}$ and $^4S_{3/2}$ states by organic ligands and/or water molecules. Nevertheless, the red ($^4F_{9/2} \rightarrow {}^4I_{15/2}$) emission band remained almost unchanged. This band is most critical for biological imaging, because red light is much less absorbed by endogenous chromophores.

Example 5

In Vivo Depth-Resolved Microscopic Imaging

Two-photon laserscanning microscopy (2P LSM) is one of today's tools of choice for functional physiological imaging with submicron resolution. Multiphoton excitation offers several advantages over linear methods, such as improved depth resolution and reduced risk for photodamage. However, 2P LSM typically requires extremely high local fluxes to compensate for generally low two-photon absorption cross-sections of fluorescent chromophores. Such fluxes are attainable through the use of expensive pulsed femtosecond lasers, which dramatically increase costs associated with this imaging method. Given that emission of UCNP/dendrimers can be induced by inexpensive CW lasers, we designed our experiments to compare the performance of UCNP/C1-Glu$^4$ in in vivo two-photon microscopy of mouse cerebral vasculature against regular vascular fluorescent probes.

First, a solution of dextran-conjugated fluorescein was injected into the mouse vasculature, the laser was mode-locked at 800 nm, and a stack of 200 images (512×512 pixels) spanning depths from 0 to 400 µm was acquired. The dwell time was 4 µs per pixel. The resulting maximum intensity projection (MIP) image of a 200-nm thick upper portion of the stack (FIG. 15C) depicts a section of the vascular bed of the brain cortex. At a 10-mW average power, the peak pulse power in these experiments was $\sim 1.25 \times 10^3$ W, corresponding to the photon flux of $\sim 5.0 \times 10^{27}$ photons per second per square centimeter in the beam focus ($\sim 1$ µm in diameter).

Secondly, we lowered the power of the laser pump and turned off active mode-locking, converting the Ti: sapphire into a CW source. Several image planes were scanned at both 800- and 980-nm wavelengths, showing complete absence of emission, consistent with inability to excite FITC fluorescence in a two-photon regime at low photon fluxes.

Figure 15:
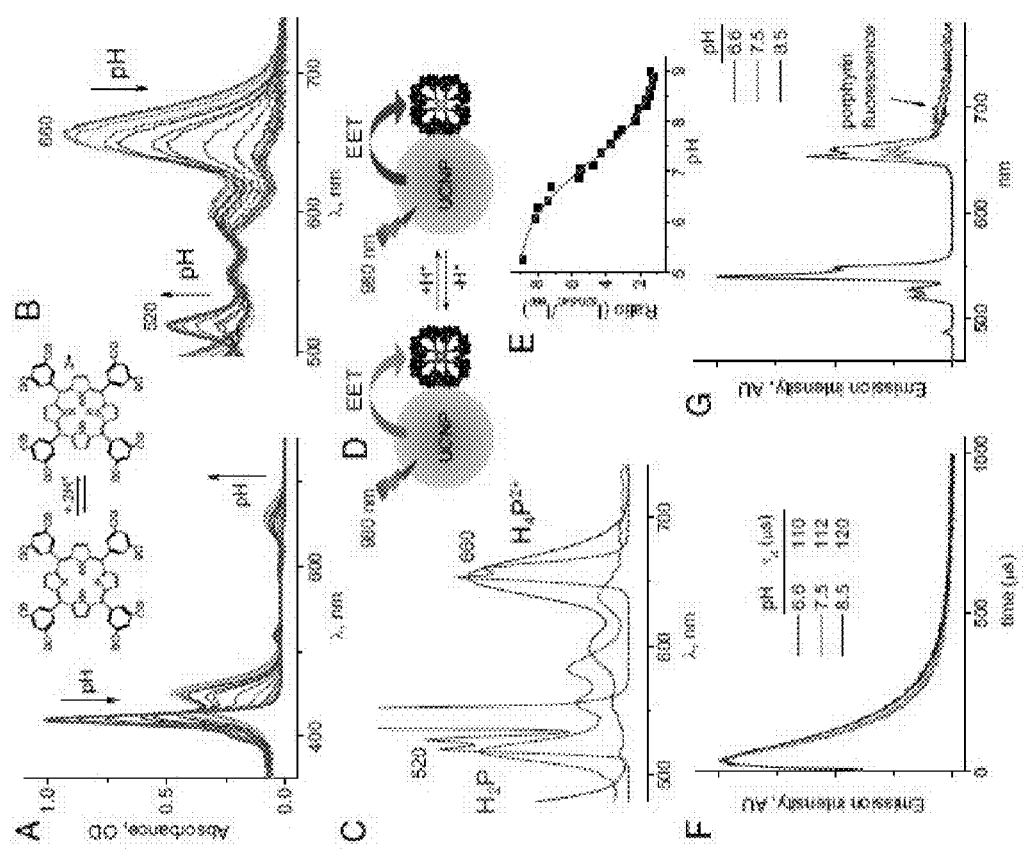
FIG. 15 shows (A and B) Changes in the absorption spectra of porphyrin-dendrimer P-Glu$^4$ with change in pH. (C) Q bands of free-base porphyrin H2P (red) and porphyrin dication H4P$^{2+}$ (blue) overlap with emission bands of UCNP. (D) Schematic diagram illustrating pH sensing by UCNP/P-Glu$^4$ via upconversion and EET. (E) pH-titration curve obtained by rationing integrated intensities of UCNP/P-Glu$^4$ transitions at 520-540 nm and 660 nm ($\lambda_{ex}$=980 nm). (F) Time-resolved emission traces of UCNP/P-Glu$^4$ at 660 nm recorded upon pulsed excitation at 980 nm at three different pH levels. (G) Steady-state emission spectra for the same three samples.

A solution of UCNP/C1-Glu4 (50 µL; 200 mg/mL) was then injected into the mouse blood (final concentration, ~3.3 mg/ml), and the same stack of images (0-400 nm) was scanned using 980 nm for excitation. Remarkably, the 3D contrast was fully regained (FIG. 15D), and the images appeared to match those obtained with FITC at all imaging depths, albeit the laser now operated in CW mode. The pixel dwell time was increased up to 20 ns to avoid smearing in the scanning direction attributable to the long emission lifetimes of UCNPs (FIG. 15E). Smearing at high scan speeds can be reduced by using confocal pinholes; however, this leads to rejection of a large portion of valuable signal. Importantly, the excitation power was kept as low as 1.5-1.7 mW (i.e., $\sim 8 \times 10^5$ times times lower than the peak power in the pulsed operation), resulting in the flux of only $\sim 7.4 \times 10^{21}$ photons per second per square centimeter through the same focal cross-section ($\sim 1$ µm in diameter).

No obvious signs of toxicity could be observed upon intravascular administration of UCNPs. During the entire imaging procedure, the heart rate and blood pressure of the mouse remained normal. As the acquisition progressed, the signal gradually faded as the probe was removed from the circulation, presumably because of the uptake by the liver and/or excretion through the kidneys. To maintain adequate signal, we administered additional 50 µL of the probe solution. Neither that nor the previous injection showed any effect on the physiological status of the animal. An additional four mice were tested by injecting similar probe doses, also not showing any signs of toxicity. The behavior of the animals on the following day appeared normal. Based on these observations, we conclude that UCNP/C1-Glu$^4$ can be safely used as a vascular multiphoton probe.

Previous attempts to use UCNP-based materials in tissue multiphoton microscopy were either performed in wide field, and, thus, did not achieve depth resolution, or required substitution of the entire blood volume with solution of imaging nanoparticles to attain adequate signal levels, thus not occurring truly in vivo. Despite large loads of the probe, the reported scan speeds (e.g., 200 ns per pixel) and resolution (e.g., 25 nm in Z) were significantly lower than typically achieved in two-photon microscopy. In contrast, UCNP/dendrimers made it possible to perform truly in vivo depth-resolved, high-resolution imaging with CW sources at adequate scan rates and probe concentrations.

Example 6

Excitation Energy Transfer: Application in pH Sensing

Excitation energy transfer (EET) from UCNPs to auxiliary chromophores provides a convenient way of coupling upconversion to various functions performed by these chromophores. For example, upconversion/EET has been used to quantify interactions of functionalized UCNPs with binding partners, shift emission wavelength for deeper tissue imaging, and construct upconverting singlet oxygen sensitizers and solid-state sensors. When the core of a dendrimer attached to the UCNP surface can perform simultaneously as an optical probe for a specific analyte, UCNP-to-dendrimer EET should enable analyte sensing via upconverted luminescence, whereby UCNPs play the role of low-flux multiphoton antennae in contrast to high-flux sensitization in dendritic systems with conventional antenna chromophores.

Polyglutamic porphyrin-dendrimers have been shown in the past to operate as efficient probes for pH in microheterogeneous systems. Porphyrin spectra undergo dramatic changes upon protonation (FIGS. 15A and B). Q11 band ($\lambda$max=520 nm) of free-base porphyrin ($H_2P$) overlaps with $^2H_{1\ 1/2} \rightarrow {}^4I_{1\ 5/2}$ emission of $Er^{3+}$ ion (FIG. 15E), whereas Q00 band of the porphyrin dication $H_4P^{2+}$ ($\lambda$max~660 nm) overlaps with $^4F_{9/2} \rightarrow {}^4I_{1\ 5/2}$ emission band (FIG. 15C). Porphyrin transitions have large oscillator strengths, thereby acting as acceptors of UCNP luminescence, so that the green and red emission bands are attenuated differently depending on the protonation state of the porphyrin (FIG. 15D). By exciting UCNP/P-Glu$^4$ near 980 nm and rationing the visible UCNP emission bands, a ratiometric protonation curve can be constructed.

To demonstrate this principle (FIGS. 15D and E), small portions of aqueous HCl were added to a solution of UCNP/P-Glu$^4$, which led to a gradual change in the red/green emission ratio. The resulting sigmoidal plot (FIG. 15E) provides an analytical curve for pH, whereby the signal is obtained via multiphoton upconversion. One key advantage of this sensing approach is that the probe itself (porphyrin in our case) does not have to be emissive, which greatly expands the selection of potential sensing chromophores. Secondly, the scheme can be extended on virtually any analyte as long as the optical transitions of the chromophore overlaps with emission bands of UCNP. Compared with conventional macromolecular pH probes [e.g., seminaphthorhodafluor (SNARF)—dextrans; Invitrogen], UCNPs can be excited by low-power nearinfrared sources. For example, upon direct injection into the tissue interstitial space, UCNP/dendrimers may be used for mapping of pH in hypoxic tumors, including high-resolution twophoton microscopic measurements.

Time-resolved emission intensity profiles ($\lambda em=660$ nm) were recorded at three different pH values upon excitation of UCNP/PGlu$^4$ using 980-nm laser pulses (FIG. 15H). The curves comprise characteristic rise and decay phases, corresponding to the sensitization and subsequent decay of the $Er^{3\pm-}$ excited state. The decay lifetimes ($\tau d$) appear to only weakly depend of pH, whereas the integrated intensity of the red transition decreases ca. 40% from basic (least overlap with porphyrin) to acidic (most overlap with porphyrin) state (FIG. 15J). This result suggests that the EET in the UCNP/P-Glu$^4$ system occurs predominantly via the "trivial" emission-reabsorption mechanism, whereas only a small fraction of the energy is transferred by way of non-radiative-type interaction. Indeed, in the case of a nonradiative mechanism, UCNP decay lifetimes would be scaled proportionally to the integrated intensities. Emission-reabsorption is consistent with rather large separation between the emitting ions within the nanocrystal lattice and the surface-adhered porphyrin-dendrimers. The fluorescence quantum yield of the porphyrin (pH 9) of UCNP/P-Glu$^4$ was found to be nearly the same as that of free PGlu$^4$ in solution (fl~0.025), whereas the shifts in the absorption and emission spectra of the porphyrin in UCNP/P-Glu$^4$ indicate interaction between the dendrimer, nanoparticle surface, and possibly other neighboring dendrimers. A change in the intensity of a shoulder near 700 nm (FIG. 15J), occurring with change in pH, suggests that this emission originates from the porphyrin and is excited via upconversion.

In conclusion, we reported dendrimerization as an efficient ligand-exchange method leading to soluble upconverting nanoparticles formultiphoton imaging and sensing. By using dendrimers with optically active cores, UCNPs can be transformed into upconverting ratiometric sensors for specific analytes, such as pH. Excellent solubility and lack of apparent toxicity of dendritic UCNPs enabled in vivo depth-resolved, high-resolution imaging of tissue with CW laser sources using photon fluxes almost $10^6$ times lower that typically used in two-photon imaging.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A composition comprising a plurality of dendrimerized nanoparticles comprising a plurality of nanoparticles each having a surface coated with a plurality of dendrite polymers, wherein each dendrite polymer comprises a core, with a plurality of dendrons, said dendrons comprise a focal point that is attached to the core and from which its branches extend to form a peripheral surface having ionic hydrophilic groups, wherein the nanoparticle surface is linked to the peripheral surface of the dendrite polymers having ionic hydrophilic groups, and wherein said composition is water-soluble.

2. The composition of claim 1, wherein the diameter of each nanoparticle ranges from about 2 nm to about 150 nm.

3. The composition of claim 1, wherein said nanoparticle is an up-converting nanoparticle (UCNP).

4. The composition of claim 3, wherein said nanoparticle is a lanthanide-based up-converting nanoparticle.

5. The composition of claim 1, wherein said nanoparticle is a down-converting nanoparticle.

6. The composition of claim 1, wherein said nanoparticle is a metal nanoparticle.

7. The composition of claim 6, wherein said nanoparticle is an iron-oxide nanoparticle.

8. The composition of claim 7, wherein said dendrite polymer is a dendrimer.

9. A composition comprising a plurality of nanoparticles, wherein the surface of each nanoparticle is dendrimerized by linking to a dendrite polymer having a hydrophilic group or a hyperbranched polymer having a hydrophilic group, and wherein said composition is water-soluble, wherein said nanoparticle is a metal nanoparticle, wherein said metal nanoparticle is an iron-oxide nanoparticle, wherein said dendrite polymer is a dendrimer, and wherein said dendrimer is a polyglutamic dendrimer.

10. The composition of claim 9, wherein said polyglutamic dendrimer comprises a pH sensitive core.

11. The composition of 10, wherein said pH sensitive core is meso-3,5-dialkoxyarylporhyrin (P).

12. The composition of claim 9, wherein said polyglutamic dendrimer comprises a 4,4',4'',4''',4'''',4''''',4'''''',4'''''''((4-tetrayltetrakis[ethyn-1,2-diylbenzene-5,1,3-triylbis(carbonylimino)]))octabutanoic acid (C1) core.

13. The composition of claim 1, wherein at least one nanoparticle is linked to a ligand, wherein the ligand is specific for a biological target.

14. The composition of claim 1, wherein at least one nanoparticle is linked to a liposome, a macromolecule, a peptide, a protein, a chelating agent, a nucleic acid, a polylysine, a dextran, or a combination thereof.

15. The composition of claim 1, wherein said nanoparticle is linked to said dendrite polymer or said hyperbranched polymer by ligand exchange linkage.

16. The composition claim 1, wherein said nanoparticle is covalently linked to said dendrite polymer or said hyperbranched polymer.

17. The composition of claim 1, wherein said composition comprises a cross-linking agent that links said each nanoparticle to said dendrite polymer or said hyperbranched polymer.

18. The composition of claim 17, wherein said cross-linking agent is a homobifunctional crosslinker, a heterobifunctional cross-linker, a linear polymer, a branched polymer, a nanoparticle, a nucleic acid, a peptide, a protein, or a combination thereof.

19. The composition of claim 17, wherein said cross-linking agent has a thiol reactive moiety.

20. An imaging agent comprising the composition claim 1.

21. A method of obtaining an image in a subject, comprising administering to said subject the composition of claim 1; imagining said subject.

22. The method of claim 21, wherein said image is a magnetic resonance image (MRI).

23. The method of claim 21, wherein said image is an in vivo two-photon microscopy image.

24. A method of measuring the presence of an analyte in a sample, the method comprising contacting said sample with the composition of claim 1, wherein said dendrite polymers or hyperbranched polymers comprise an analyte-sensitive core that signals the presence of said analyte.

25. The method of claim 24, wherein said sample is a biological sample.

26. The method of claim 24, wherein the method of measuring said analyte in said sample further comprises visually measuring the emission spectra of said composition.

27. The method of claim 26, wherein the step of measuring the emission spectra of said composition further comprises rationing the visible bands of said UCNP.

28. The method of claim 27, wherein a ratiometric protonation curve is generated from rationing said visible UCNP bands.

29. The method of claim 24, wherein said analyte is measured in interstitial tissue space in a subject.

30. The method of claim 29, wherein said subject is human.

31. The method of claim 29, wherein said composition is administered to said subject by direct injection.

32. The method of claim 29, further comprises the step of mapping of pH in hypoxic tumors.

* * * * *